(12) United States Patent
Frost et al.

(10) Patent No.: US 10,890,570 B2
(45) Date of Patent: Jan. 12, 2021

(54) GAS MEASUREMENT DEVICE

(71) Applicant: MICHIGAN TECHNOLOGICAL UNIVERSITY, Houghton, MI (US)

(72) Inventors: Megan Frost, Houghton, MI (US); Weilue He, Houghton, MI (US)

(73) Assignee: MICHIGAN TECHNOLOGICAL UNIVERSITY, Houghton, MI (US)

( * ) Notice: Subject to any disclaimer, the term of this patent is extended or adjusted under 35 U.S.C. 154(b) by 210 days.

(21) Appl. No.: 16/203,296

(22) Filed: Nov. 28, 2018

(65) Prior Publication Data

US 2019/0162709 A1    May 30, 2019

Related U.S. Application Data

(60) Provisional application No. 62/592,323, filed on Nov. 29, 2017.

(51) Int. Cl.
| | | |
|---|---|---|
| *G01N 33/00* | (2006.01) | |
| *G01N 33/48* | (2006.01) | |
| *B01D 69/12* | (2006.01) | |
| *B01D 71/34* | (2006.01) | |
| *B01D 53/22* | (2006.01) | |
| *G01N 30/86* | (2006.01) | |
| *B01D 69/10* | (2006.01) | |
| *B01D 71/74* | (2006.01) | |

(Continued)

(52) U.S. Cl.
CPC ....... *G01N 33/0027* (2013.01); *B01D 53/228* (2013.01); *B01D 69/10* (2013.01); *B01D 69/12* (2013.01); *B01D 71/34* (2013.01); *B01D 71/70* (2013.01); *B01D 71/74* (2013.01); *C08J 7/0427* (2020.01); *G01N 30/8665* (2013.01); *G01N 33/0037* (2013.01)

(58) Field of Classification Search
CPC .......... B01D 53/228; B01D 53/30; B01D 69/00-14; B01D 71/00-82; C08J 7/0427; G01N 30/8665; G01N 33/00; G01N 33/0027; G01N 33/0037; G01N 33/48-50
See application file for complete search history.

(56) References Cited

U.S. PATENT DOCUMENTS

| | | | |
|---|---|---|---|
| 6,083,393 A * | 7/2000 | Wu | B01D 67/0006 |
| | | | 210/500.27 |
| 2018/0319943 A1 * | 11/2018 | Liu | C09D 169/00 |

FOREIGN PATENT DOCUMENTS

| | | | | |
|---|---|---|---|---|
| DE | 19507584 A1 * | 9/1996 | | B01D 67/009 |
| JP | 2010214324 A * | 9/2010 | | B01D 71/34 |

OTHER PUBLICATIONS

A. Chaux, et al., Perivascular delivery of a nitric oxide donor inhibits neointi-mal hyperplasia in vein grafts implanted in the arterial circulation, J. Thorac. Cardiovasc. Surg. 115 (3) (1998) 604-614.

(Continued)

*Primary Examiner* — Nguyen Q. Ha
(74) *Attorney, Agent, or Firm* — Michael Best & Friedrich LLP

(57) ABSTRACT

A device including a first chamber, a second chamber, and a membrane permeable to neutral gases but impermeable to water that is positioned between the first chamber and the second chamber. The membrane includes a first layer including PVDF and PDMS, and the PVDF has a plurality of pores at least partially filled with at least some of the PDMS.

17 Claims, 16 Drawing Sheets
(16 of 16 Drawing Sheet(s) Filed in Color)

(51) Int. Cl.
   B01D 71/70       (2006.01)
   C08J 7/04        (2020.01)

(56) References Cited

OTHER PUBLICATIONS

A. Fontijn, A.J. Sabadell, R.J. Ronco, Homogeneous chemiluminescent mea-surement of nitric oxide with ozone. Implications for continuous selective monitoring of gaseous air pollutants, Anal. Chem. 42 (6) (1970) 575-579.
A.J. Dunham, R.M. Barkley, R.E. Sievers, Aqueous nitrite ion determination by selective reduction and gas phase nitric oxide chemiluminescence, Anal. Chem. 67 (1) (1995) 220-224.
A.S.Vidwans, et al., Analysis of the neuroprotective effects of various nitric oxide donor compounds in murine mixed cortical cell culture, J. Neurochem. 72 (5) (1999) 1843-1852.
Armstrong et al., Diabetic foot ulcers and their recurrence. N. Engl. J. Med. 2017, 376, 2367-2375.
Atlas, Brussels, Belgium: International Diabetes Federation; International Diabetes Federation (IDF): Brussels, Belgium, 2017.
B. Mellion, et al., Evidence for the inhibitory role of guanosine 3',5'-mono-phosphate, Blood 57 (1981) 5.
B.G. Hill, et al., What part of NO don't you understand? Some answers to the cardinal questions in nitric oxide biology, J. Biol. Chem. 285 (26) (2010) 19699-19704.
B.J. Nablo, A.R. Rothkley, M.H. Schoenfisch, Nitric oxide-releasing sol-gels as antibacterial coatings for orthopedic implants, Biomaterials 26 (8) (2005) 917-924.
B.J. Privet J.H. Shin, M.H. Schoenfisch, Electrochemical nitric oxide sensors for physiological measurements, Chem. Soc. Rev. 39 (6) (2010) 1925-1935.
B.W. Allen, J. Liu, C.A. Piantadosi, Electrochemical detection of nitric oxide in biological fluids, Methods Enzym. 396 (2005) 68-77.
B.Y. Owusu, R. Stapley, R.P. Patel, Nitric oxide formation versus scavenging: the red blood cell balancing act, J. Physiol. 590 (20) (2012) 4993-5000.
Beaglehole et al., UN high-level meeting on non-communicable diseases: Addressing four questions. Lancet 2011, 378, 449-455.
Bradford, A rapid and sensitive method for the quantitation of microgram quantities of protein utilizing the principle of protein-dye binding. Anal. Biochem. 1976, 72, 248-254.
Brecher, The fibroblast and nitric oxide. In Nitric Oxide and the Cardiovascular System, Loscalzo, J., Vita, J.A., Eds.; Humana Press: Totowa, NJ, USA, 2000; pp. 177-189.
Bryan et al., Methods to detect nitric oxide and its metabolites in biological samples. Free Radic. Biol. Med. 2007, 43, 645-657.
C. Wang, W.M. Deen, Nitric oxide delivery system for cell culture studies, Ann. Biomed. Eng. 31 (1) (2003) 65-79.
C. Xu, et al., In vitro study of human vascular endothelial cell function on materials with various surface roughness, J. Biomed. Mater. Res. Part A 71A (1)(2004) 154-161.
C.-Q. Li, G.N. Wogan, Nitric oxide as a modulator of apoptosis, Cancer Lett. 226 (1) (2005) 1-15.
Cosentino et al., High glucose increases nitric oxide synthase expression and superoxide anion generation in human aortic endothelial cells. Circulation 1997, 96, 25-28.
D. Giustarini, et al., Nitrite and nitrate measurement by Griess reagent in human plasma: evaluation of interferences and standardization, Methods Enzym. 440 (2008) 361-380.
D. Tsikas, Review Methods of quantitative analysis of the nitric oxide metabolites nitrite and nitrate in human biological fluids, Free Radic. Res. 39 (8)(2005) 797-815.
D. Yao, A.G. Vlessidis, N.P. Evmiridis, Determination of nitric oxide in biological samples, Microchim. Acta 147 (1-2) (2004) 1-20.
D.D. Thomas, et al., Hypoxic inducible factor 1α, extracellular signal-regulated kinase, and p53 are regulated by distinct threshold concentrations of nitric oxide, Proc. Natl. Acad. Sci. USA 101 (24) (2004) 8894-8899.
D.D. Thomas, et al., The chemical biology of nitric oxide: implications in cellular signaling, Free Radic. Biol. Med. 45 (1) (2008) 18-31.
F. Bedioui, N. Villeneuve, Electrochemical nitric oxide sensors for biological samples—principle, selected examples and applications, Electroanalysis 15 (1)(2003) 5-18.
Falanga, Wound healing and its impairment in the diabetic foot. Lancet 2005, 366, 1736-1743.
Feelisch et al., "Methods in Nitric Oxide Research," Chapter 21: Determination of Nitric Oxide by the Chemiluminescence Reaction with Ozone, Wiley-Blackwell: Oxford, UK, 1996.
Frykberg et al., Challenges in the treatment of chronic wounds. Adv. Wound Care 2015, 4, 560-582.
G.A. Blaise, et al., Nitricoxide, cell signaling and cell death, Toxicology 208 (2) (2005) 177-192.
G.E. Romanowicz, M. Nielsen, M.C. Frost, S-Nitroso-N-acetyl-d-penicillamine covalently linked to polydimethylsiloxane (SNAP-PDMS) for use as a controlled photoinitiated nitric oxide release polymer, Sci. Technol. Adv. Mater. 12 (5) (2011) 055007.
Grisham et al., Physiological chemistry of nitric oxide and its metabolites: Implications in inflammation. Am. J. Physiol. Gastrointest. Liver Physiol. 1999, 276, G315-G321.
Guzik et al., Nitric oxide and superoxide in inflammation. J. Physiol. Pharmacol. 2003, 54, 469-487.
H. Lee, et al., Mussel-inspired surface chemistry for multifunctional coatings, Science 318 (5849) (2007) 426.
H. Zhang, et al., Nitric oxide releasing silicone rubbers with improved blood compatibility: preparation, characterization, and in vivo evaluation, Bioma-terials 23 (6) (2002) 1485-1494.
H.A. Moynihan, S.M. Roberts, Preparation of some novel S-nitroso compounds as potential slow-release agents of nitric oxide in vivo, J. Chem. Soc. Perkin Trans. 1 (7) (1994) 797-805.
Halliwell, Cell culture, oxidative stress, and antioxidants: Avoiding pitfalls. Biomed. J. 2014, 37, 99.
He et al., CellNO trap: Novel device for quantitative, real-time, direct measurement of nitric oxide from cultured RAW267.4 macrophages. Redox Biol. 2016, 8, 383-397.
He et al., Direct measurement of actual levels of nitric oxide (NO) in cell culture conditions using soluble NO donors. Redox Biol. 2016, 9, 1-14.
Hetrick et al., Analytical chemistry of nitric oxide. Annu. Rev. Anal. Chem. 2009, 2, 409-433.
Hoshiyama et al., Effect of high glucose on nitric oxide production and endothelial nitric oxide synthase protein expression in human glomerular endothelial cells. Nephron Exp. Nephrol. 2003, 95, e62-e68.
Houreld et al., Irradiation at 830 nm stimulates nitric oxide production and inhibits pro-inflammatory cytokines in diabetic wounded fibroblast cells. Lasers Surg. Med. 2010, 42, 494-502.
Hunter et al., Inaccuracies of nitric oxide measurement methods in biological media. Anal. Chem. 2013, 85, 1957-1963.
Ii et al., Neuronal nitric oxide synthase mediates statin-induced restoration of vasa nervorum and reversal of diabetic neuropathy Circulation 2005, 112, 93-102.
Inzucchi, Diagnosis of diabetes. N. Engl. J. Med. 2012, 367, 542-550.
J. Umans, R. Levi, Nitric oxide in the regulation of blood flow and arterial pressure, Annu. Rev. Physiol. (1995) 771-790.
J.N. Bates, Nitric oxide measurement by chemiluminescence detection, Neu-roprotocols 1 (2) (1992) 141-149.
J.R. Lancaster, A tutorial on the diffusibility and reactivity of free nitric oxide, Nitric Oxide 1 (1) (1997) 18-30.
J.R. Lancaster, Simulation of the diffusion and reaction of endogenously pro-duced nitric oxide, Proc. Natl. Acad. Sci. 91 (17)(1994) 8137-8141.
Jorens et al., Synergism between interleukin-1 beta and interferon-gamma, an inducer of nitric oxide synthase, in rat lung fibroblasts. Eur. J. Pharmacol. 1992, 224, 7-12.
K.A. Mowery, M.E Meyerhoff, The transport of nitric oxide through various polymeric matrices, Polymer 40 (22) (1999) 6203-6207.
K.S. Bohl, J.L. West, Nitric oxide-generating polymers reduce platelet adhesion and smooth muscle cell proliferation, Biomaterials 21 (22) (2000) 2273-2278.

(56) References Cited

OTHER PUBLICATIONS

Kirsner et al., Advanced biological therapies for diabetic foot ulcers. Arch. Dermatol. 2010, 146, 857-862.
Kisselbach et al., CD90 expression on human primary cells and elimination of contaminating fibroblasts from cell cultures. Cytotechnology 2009, 59, 31-44.
Kopincová et al., Biochemical aspects of nitric oxide synthase feedback regulation by nitric oxide. Interdisciplin. Toxicol. 2011, 4, 63-68.
Kwesiga et al., "Investigative Study on Nitric Oxide Production in Human Dermal Fibroblast Cells under Normal and High Glucose Conditions," Medical Sciences, 2018, 6(4):99.
L.A. Ridnour, et al., Molecular mechanisms for discrete nitric oxide levels in cancer, Nitric Oxide 19 (2) (2008) 73-76.
L.K. Keefer, Progress toward clinical application of the nitric oxide-releasing diazeniumdiolates 1, Annu. Rev. Pharmacol. Toxicol. 43 (1) (2003) 585-607.
Leung, Diabetic foot ulcers—A comprehensive review. Surgeon 2007, 5, 219-231.
Loots, Fibroblasts derived from chronic diabetic ulcers differ in their response to stimulation with EGF, IGF-I, bFGF and PDGF-AB compared to controls. Eur. J. Cell Biol. 2002, 81, 153-160.
Luo et al., Nitric oxide: A newly discovered function on wound healing. Acta Pharmacol. Sin. 2005, 26, 259-264.
M. Starrett, et al., Wireless platform for controlled nitric oxide releasing op-tical fibers for mediating biological response to implanted devices, Nitric Oxide 27 (4) (2012) 228-234.
M.B. Grisham, D. Jourd'Heuil, D.A. Wink, I. Physiological chemistry of nitric oxide and its metabolites: implications in inflammation, Am. J. Physiol.—Gastrointest. Liver Physiol. 276 (2) (1999) G315-G321.
M.G. Frost, et al., In vivo biocompatibility and analytical performance of in-travascular amperometric oxygen sensors prepared with improved nitric oxide-releasing silicone rubber coating, Anal. Chem. 4 (23) (2002) 5942-5947.
M.C. Frost, M.M. Reynolds, M.E. Meyerhoff, Polymers incorporating nitric oxide releasing/generating substances for improved biocompatibility of blood-con-tacting medical devices, Biomaterials 26 (14) (2005) 1685-1693.
M.M. Reynolds, M.C. Frost, M.E. Meyerhoff, Nitric oxide-releasing hydrophobic polymers: preparation, characterization, and potential biomedical applica-tions, Free Radic. Biol. Med. 37 (7) (2004) 926-936.
M.P. Chin, D.B. Schauer, W.M. Deen, Nitric oxide, oxygen, and superoxide formation and consumption in macrophages and colonic epithelial cells, Chem. Res. Toxicol. 23 (4) (2010) 778-787.
M.T. Gladwin, et al., Relative role of heme nitrosylation and β-cysteine 93 nitrosation in the transport and metabolism of nitric oxide by hemoglobin in the human circulation, Proc. Natl. Acad. Sci. 97 (18) (2000) 9943-9948.
M.W. Radomski, R. Palmer, S. Moncada, The anti-aggregating properties of vascular endothelium: interactions between prostacyclin and nitric oxide, Br. J. Pharmacol. 92 (3) (1987) 639.
Mansbridge et al., Growth factors secreted by fibroblasts: Role in healing diabetic foot ulcers. Diabetes Obes. Metab. 1999, 1, 265-279.
Mills et al., Macrophages at the fork in the road to health or disease. Front. Immunol. 2015, 6, 59.
Mosmann, Rapid colorimetric assay for cellular growth and survival: Application to proliferation and cytotoxicity assays. J. Immunol. Methods 1983, 65, 55-63.
Moulik et al., Amputation and mortality in new-onset diabetic foot ulcers stratified by etiology. Diabetes Care 2003, 26, 491-494.
N. Nalwaya, W.M.D. Deen, Nitric oxide, oxygen, and superoxide formation and consumption in macrophage cultures, Chem. Res. Toxicol. 18 (3) (2005) 486-493.
N.S. Bryan, M.B. Grisham, Methods to detect nitric oxide and its metabolites in biological samples, Free Radic. Biol. Med. 43 (5) (2007) 645-657.
Organization, W.H. Global Report on Diabetes; World Health Organization: Geneva, Switzerland, 2016.
Organization,W.H. Global Action Plan for the Prevention and Control of Noncommunicable Diseases 2013-2020; World Health Organization: Geneva, Switzerland, 2013.
Pacher et al., Nitric oxide and peroxynitrite in health and disease. Physiol. Rev. 2007, 87, 315-424.
R. Gifford, et al., Mediation of in vivo glucose sensor inflammatory response via nitric oxide release, J. Biomed. Mater. Res. Part A 75 (4) (2005) 755-766.
R.A. Hunter, et al., Inaccuracies of nitric oxide measurement methods in bio-logical media, Anal. Chem. 85 (3) (2013) 1957-1963.
R.S. Lewis, et al., Kinetic analysis of the fate of nitric oxide synthesized by macrophages in vitro. Journal of Biologcal, Chemistry 270 (49) (1995) 29350-29355.
Ralston, New global target on non-communicable diseases: A call to action for the global cardiovascular disease community. Cardiovasc. J. Afr. 2012, 23, 241-242.
Rizk et al., Nitric oxide and wound healing. World J. Surg. 2004, 28, 301-306.
S. Archer, Measurement of nitric oxide in biological models, FASEB J. 7 (2)(1993) 349-360.
S.H. Baek, et al., Augmentation of intrapericardial nitric oxide level by a pro-longed-release nitric oxide donor reduces luminal narrowing after porcine coronary angioplasty, Circulation 105 (23) (2002) 2779-2784.
S.J. Morris, Regulation of enzymes of the urea cycle and arginine metabolism, Annu. Rev. Nutr. 22 (1) (2002) 87-105.
Schäffer et al., Nitric oxide, an autocrine regulator of wound fibroblast synthetic function. J. Immunol. 1997, 158, 2375-2381.
Schneider et al., NIH image to ImageJ: 25 years of image analysis. Nat. Methods 2012, 9, 671.
Schwentker et al., Nitric oxide and wound repair: Role of cytokines? Nano Oxide 2002, 7, 1-10.
Shi, The role of iNOS in wound healing. Surgery 2001, 130, 225-229.
T. Noda, F. Amano, Differences in nitric oxide synthase activity in a macro-phage-like cell line, RAW264. 7 cells, treated with lipopolysaccharide (LPS) in the presence or absence of interferon-γ (IFN-γ): possible heterogeneity of iNOS activity, J. Biochem. 121 (1) (1997) 38-46.
Thomas et al. The chemical biology of nitric oxide: Implications in cellular signaling. Free Radic. Biol. Med. 2008, 45, 18-31.
Thomas et al., Hypoxic inducible factor 1 , extracellular signal-regulated kinase, and p53 are regulated by distinct threshold concentrations of nitric oxide. Proc. Natl. Acad. Sci. USA 2004, 101, 8894-8899.
Tracy et al., Extracellular matrix and dermal fibroblast function in the healing wound. Adv. Wound Care 2016, 5, 119-136.
V. Calabrese, et al., Nitric oxide in the central nervous system: neuroprotection versus neurotoxicity, Nat. Rev. Neurosci. 8 (10) (2007) 766-775.
Villalobo, Nitric oxide and cell proliferation. FEBS J. 2006, 273, 2329-2344.
Walsh et al. Association of diabetic foot ulcer and death in a population-based cohort from the United Kingdom. Diabet. Med. 2016, 33, 1493-1498.
Walton et al., The potential of transdermal nitric oxide treatment for diabetic peripheral neuropathy and diabetic foot ulcers. Diabetes Metab. Syndr. Clin. Res. Rev. 2018.
Wang et al., Human dermal fibroblasts produce nitric oxide and express both constitutive and inducible nitric oxide synthase isoforms. J. Investig. Dermatol. 1996, 106, 419-427.
Witte et al., Role of nitric oxide in wound repair. Am. J. Surg. 2002, 183, 406-412.
Xuan et al., High-glucose inhibits human fibroblast cell migration in wound healing via repression of bFGF-regulating UNK phosphorylation. PLoS ONE 2014, 9, e108182.
Y. Lee, et al., Improved planar amperometric nitric oxide sensor based on platinized platinum anode. 2. Direct real-time measure-

(56) References Cited

OTHER PUBLICATIONS ment of NO generated from porcine kidney slices in the presence of l-arginine, l-arginine polymers, and protamine, Anal. Chem. 76 (3) (2004) 545-551.

Z.H. Taha, Nitric oxide measurements in biological samples, Talanta 61 (1)(2003) 3-10.

* cited by examiner

FIG. 12A
FIG. 12B
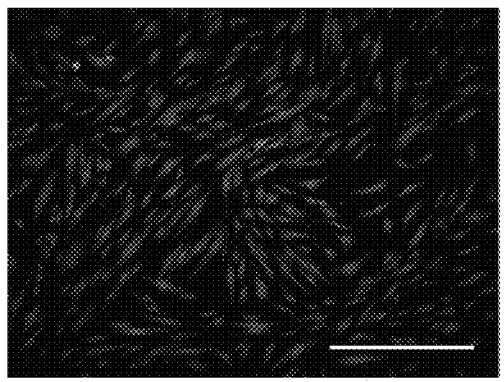
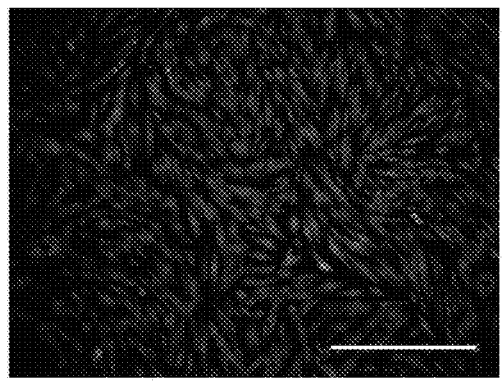
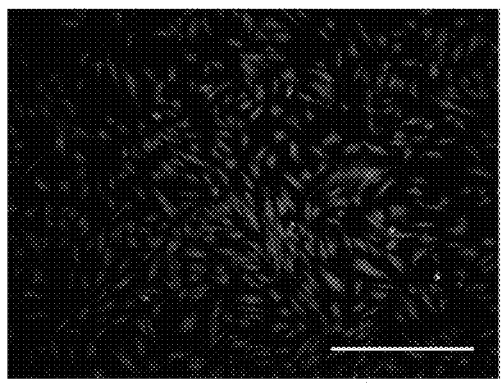
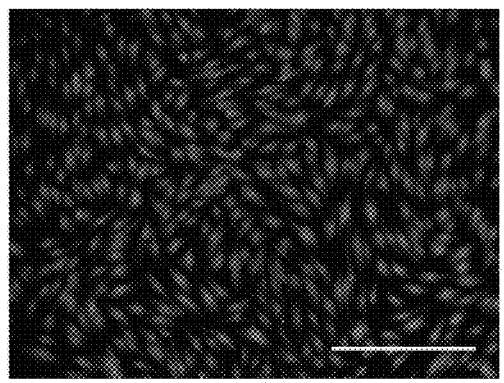
FIG. 12C
FIG. 12D

GAS MEASUREMENT DEVICE

CROSS-REFERENCE TO RELATED APPLICATION(S)

This application claims priority to U.S. Provisional Patent Application No. 62/592,323, filed on Nov. 29, 2017, the entire contents of which are fully incorporated herein by reference.

STATEMENT REGARDING FEDERALLY SPONSORED RESEARCH

This invention was made with government support under grant number DMR 1410192, awarded by the National Science Foundation. The government has certain rights in the invention.

BACKGROUND

Devices have been made for the detection and/or measurement of gases in aqueous systems, such as, for example, those used for cell culture or for diagnostic or research purposes. The detection and measurement of gases in such systems may be important to understand how the system behaves, and/or for monitoring and control of the system. Such devices may be used to measure various gases.

For example, it may be advantageous to detect and or measure Nitric Oxide (NO), in aqueous systems that are being used for cell culture. NO, which is gaseous under STP (standard temperature and pressure), is a free radical solute that serves as a key signaling molecule in many cellular processes. Nitric oxide has been shown to be a potent inhibitor of platelet adhesions and activation, plays a role in mediating the inflammatory process, and is an antibacterial agent. NO has anti-apoptotic effects in endothelial cells, lymphoma cells, ovarian follicles, cardiac myocytes and hepatocytes, and pro-apoptotic properties in macrophages, neurons, pancreatic β-cells, thymocytes chondrocytes, and hepatocytes. Some suggest that NO in low levels has a protective and proliferative effect on cells, while at high levels induces cell cycle arrest, senescence, and apoptosis. As such, the presence and/or amount of NO in a cell culture system may be very important. Moreover, devices that can be used for cell culture while also detecting and/or measuring the amount of NO in the aqueous system may be particularly advantageous.

Similarly, systems that allow for the detection and/or measurement of gases in aqueous systems can be used to observe the effects of gases on compounds and/or compositions contained within the aqueous system.

SUMMARY

In one embodiment, the invention provides a device including a first chamber, a second chamber, and a membrane permeable to neutral gases but impermeable to water that is positioned between the first chamber and the second chamber. The membrane includes a first layer including PVDF and PDMS, and the PVDF has a plurality of pores at least partially filled with at least some of the PDMS.

In another embodiment the invention provides a method for detecting or measuring the amount of a neutral gas associated with an aqueous solution, including: providing the aqueous solution in the first chamber of the aforementioned device, collecting a sample of the neutral gas from the second chamber of the device, and detecting or measuring the amount of the neutral gas in the sample with a gas measurement or gas detection device.

Other aspects of the invention will become apparent by consideration of the detailed description and accompanying drawings.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

FIG. 10A shows glass fiber filter paper; FIG. 10B shows 3 repeat of 1 g/10 ml RTV-3140 PDMS cast; FIG. 10C shows 1 cast of 1 g/10 ml RTV-3140 PDMS and 2 repeat of 1 g/8 ml RTV-3140 PDMS cast; FIG. 10D shows 1 cast of 1 g/10 ml RTV-3140 PDMS and 3 repeat of 1 g/8 ml RTV-3140 PDMS cast; FIG. 10E shows 1 cast of 1 g/10 ml RTV-3140 PDMS and 4 repeats of 1 g/8 ml RTV-3140 PDMS cast.

FIG. 12A, FIG. 12B, FIG. 12C, and FIG. 12D show images of cell viability detected by calcein AM and ethidium bromide for primary human adult dermal fibroblasts cultured in normal (5.5 mM) glucose conditions with and without stimulation (FIG. 12A, FIG. 12B) and high glucose (25 mM) conditions with and without stimulation (FIG. 12C, FIG. 12D), respectively. Scale bar 500 μm. The results are presented as the mean+/−standard deviation for n=3, *p<0.05.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Disclosed herein, among other things, is an easy and reliable device for directly measuring a neutral gas associated with an aqueous system (e.g., the flux of a neutral gas, such as $NO_{(g)}$, from cultured living cells) continuously in real-time fashion. Because of its biological and medical significance, NO is used throughout this disclosure as an exemplary neutral gas, but other neutral gases, such as $N_{2(g)}$, $CO_{2(g)}$, $O_{2(g)}$, $H_2O_{2(g)}$, $CO_{(g)}$, $H_2S_{(g)}$, $NH_{3(g)}$, and combinations thereof, are explicitly contemplated herein.

The ability of a previous device ("CellNO trap") to measure both the dose and the timing of NO generation has been verified by the same inventors in Redox Biology, 8 (2016) 383-397 and "Systematic study of the biological effects of nitric oxide (NO) using innovative NO measurement and delivery systems" Michigan Technological University, 2015, each incorporated herein by reference in their entirety.

In brief, CellNO trap was verified by using a photosensitive NO releasing material, S-nitroso-N-acetylpenicillimine modified poly-dimethylsiloxane (SNAP-PDMS). Macrophages (RAW-264.7) cells were cultured in this device and stimulated to demonstrate the ability to measure NO released from cells in a real-time, continuous manner. Additionally, retinal epithelial (ARPE-19) cells, mouse vascular smooth muscle (MOVAS) cells, vascular endothelial (SVEC) cells, L-929 cell, and mouse primary tenocyte were tested in the device to show general applicability of the device to multiple cell types.

Figure 1:
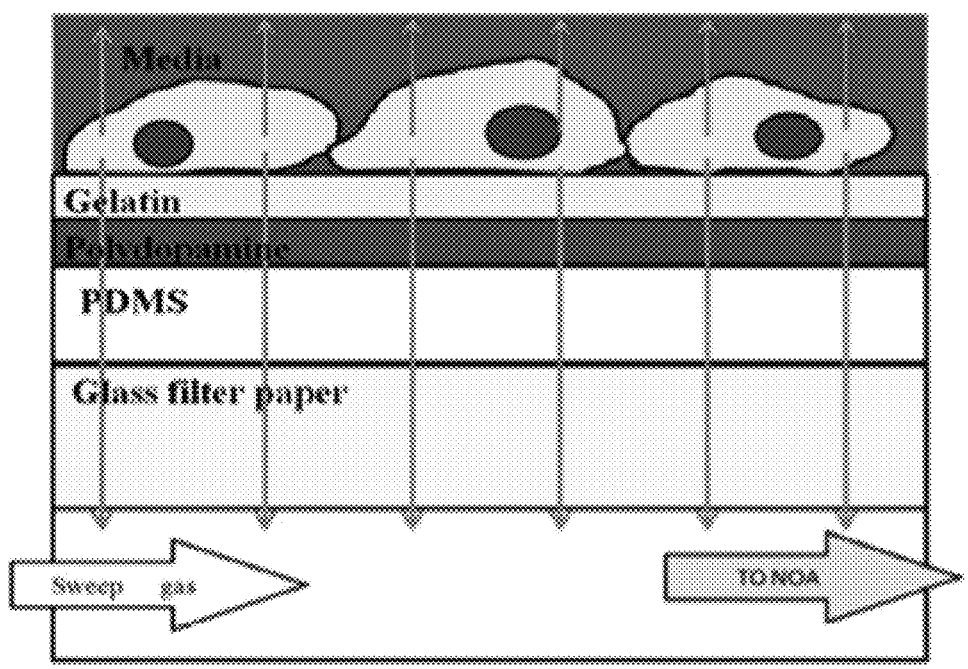
FIG. 1 shows a schematic of a gas measurement device having two chambers separated by glass filter paper coated with a layer of PDMS, a layer of polydopamine and a layer of gelatin. Cells were cultured on the gelatin top layer; cellular NO diffused in all directions; and once NO diffused through the PDMS layer into the second (lower) chamber, NO was carried into the NOA by a sweep gas for surface flux measurement.

Although the CellNO trap device advanced the state of the art, it suffers from some significant disadvantages. For example, glass fiber filter paper was used in a water tight, gas-permeable membrane (FIG. 1), but SNAP-PDMS could not be easily applied to the membrane. Additionally, the stiffness and smoothness of the membrane needed to be markedly improved to, for example, improve adhesion of cells to the membrane and the quality of fluorescent cell images.

Figure 2:
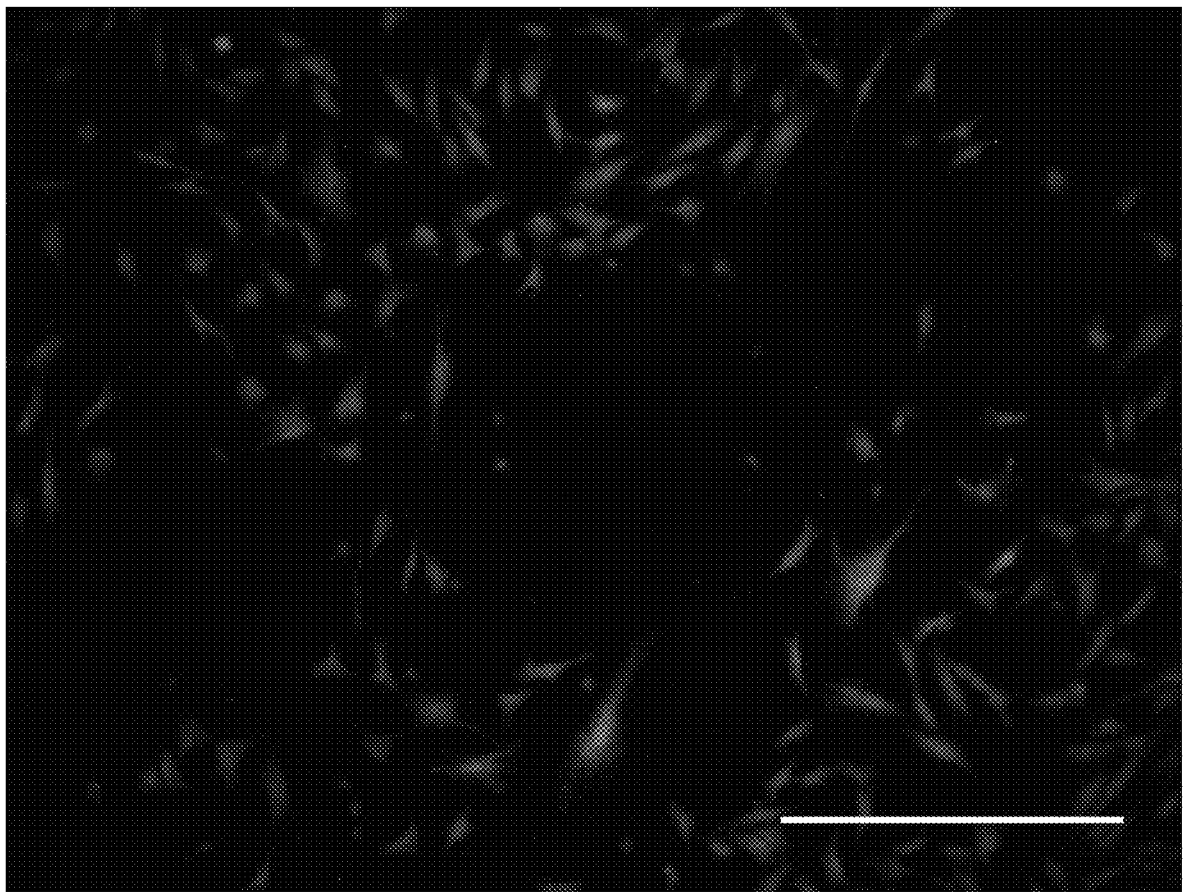
FIG. 2 shows images of live human dermal fibroblast cells (green, stained with calcein) and dead human dermal fibroblast cells (red, stained with ethidium bromide) on an area of a membrane comprising PVDF and PDMS after 48 hours of culture. Complete coating of the PVDF with PDMS was not achieved on the area where the dead cells were observed.

The unintuitive solution disclosed herein is to replace the glass-fiber filter paper in the membrane with PVDF (polyvinylidene fluoride). While PVDF has the right mechanical properties in terms of rigidity for this application, it was unknown whether PVDF could be used for measuring aqueous systems containing living cells, because PVDF is notoriously toxic to cells. It also was unknown whether coating PVDF with non-toxic PDMS would lead to cell death, and in fact, when PVDF was incompletely covered with PDMS, cell death was observed (see FIG. 2). Finally, it was unclear whether a membrane comprising PVDF and PDMS would be sufficiently gas permeable to allow for measurement of gases associated with an aqueous system by sampling the gas in a chamber on the opposite side of the membrane.

Figure 3:
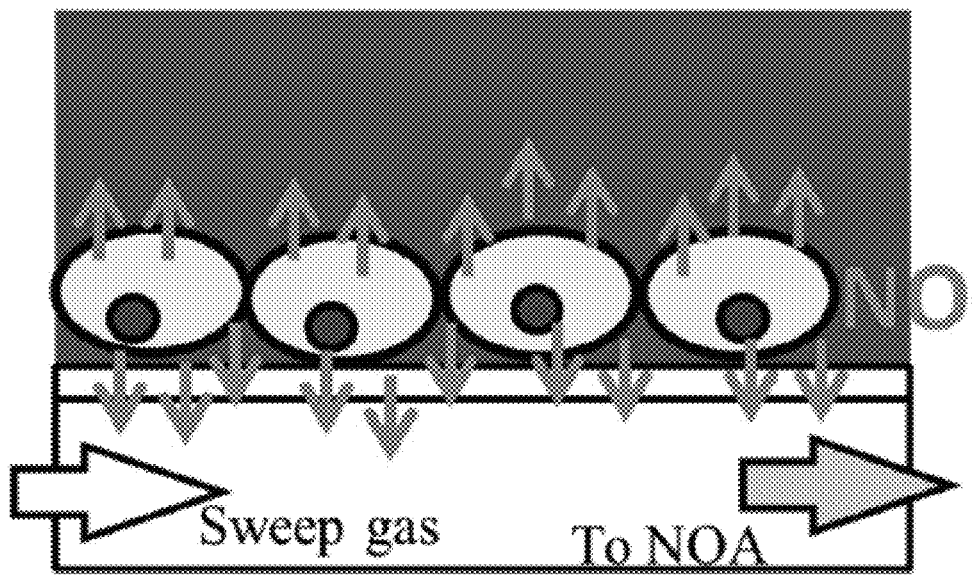
FIG. 3 shows a particular embodiment of a device of the present disclosure. It comprises two chambers (an upper and a lower chamber) separated by a membrane that is permeable to neutral gases but impermeable to water that is positioned between the first chamber and the second chamber. The membrane includes a first layer comprising PVDF and PDMS, wherein the PVDF has a plurality of pores at least partially filled with at least some of the PDMS. The first (upper) chamber contains an aqueous solution which contains living cells (e.g., cells that have been cultured). Gas associated with the cells, such NO, diffuses in all directions, including crossing the membrane into the second (lower) chamber of the device, which serves as a gas sampling chamber from which cellular NO is collected (e.g., via a sweep gas) and is detected and/or measured with a detector (e.g., via chemiluminescence).

In the disclosed device, a two-chamber structure (FIG. 3) is designed to, for example, allow cells to grow in the first (upper) chamber using conventional cell culturing media and reagents and, at the same time, sample gas phase NO, for example, in the second (lower) chamber. Once cellular NO diffuses through the interface, NO can be carried by a sweep gas into a nitric oxide analyzer (NOA) for continuous, real-time measurement.

In certain embodiments, the device has more than two chambers. In certain embodiments, the sweep gas is nitrogen or ambient air. Alternately, there may be no sweep gas, such as when a measurement or detection device is within the second chamber. Typically, the second chamber is in fluid communication with a gas detection or gas measurement device.

In certain embodiments, the gas measurement or gas detection device comprises a chemiluminescent detection device, a electrochemical detection device, an optical detection device, an infrared spectroscopy device, a mass spectrometry device, a gas chromatography device, or a quartz crystal microbalance.

In certain embodiments, the first chamber contains an aqueous solution. The aqueous solution may contain living cells. The aqueous solution may further contain a polymer. The polymer may be a hydrogel. The polymer may be adapted to release nitric oxide.

A key component of the disclosed device is a water-tight, neutral gas permeable membrane used to separate the first chamber from the second chamber. To create the two independent chambers, the membrane at a minimum needs to be 1) highly permeable to neutral gas (e.g. NO), 2) water impermeable, and 3) able to be readily fabricated. In certain embodiments, the membrane must also be 4) compatible with cell growth.

Polydimethoxylsiloxane (PDMS) is a preferred component of the membrane, because it has a large NO diffusion coefficient (up to $3.0 \times 10^{-5}$ cm$^2$/s), is highly hydrophobic such that it is impermeable to water, can be modified to be biocompatible, and is easy to cast into any shape. PDMS can be cast into layers up to 20 mm thick, such that NO diffuses through the membrane within one second. This ensures that the detection data directly reflects the real-time neutral gas released from (or consumed by) the cell layer.

However, since PDMS itself is not stiff enough to provide a mechanical support necessary for cell culture, PDMS was cast over PVDF. The PVDF provides mechanical strength while the PDMS creates a gas permeable, water-tight chamber.

Figure 7:
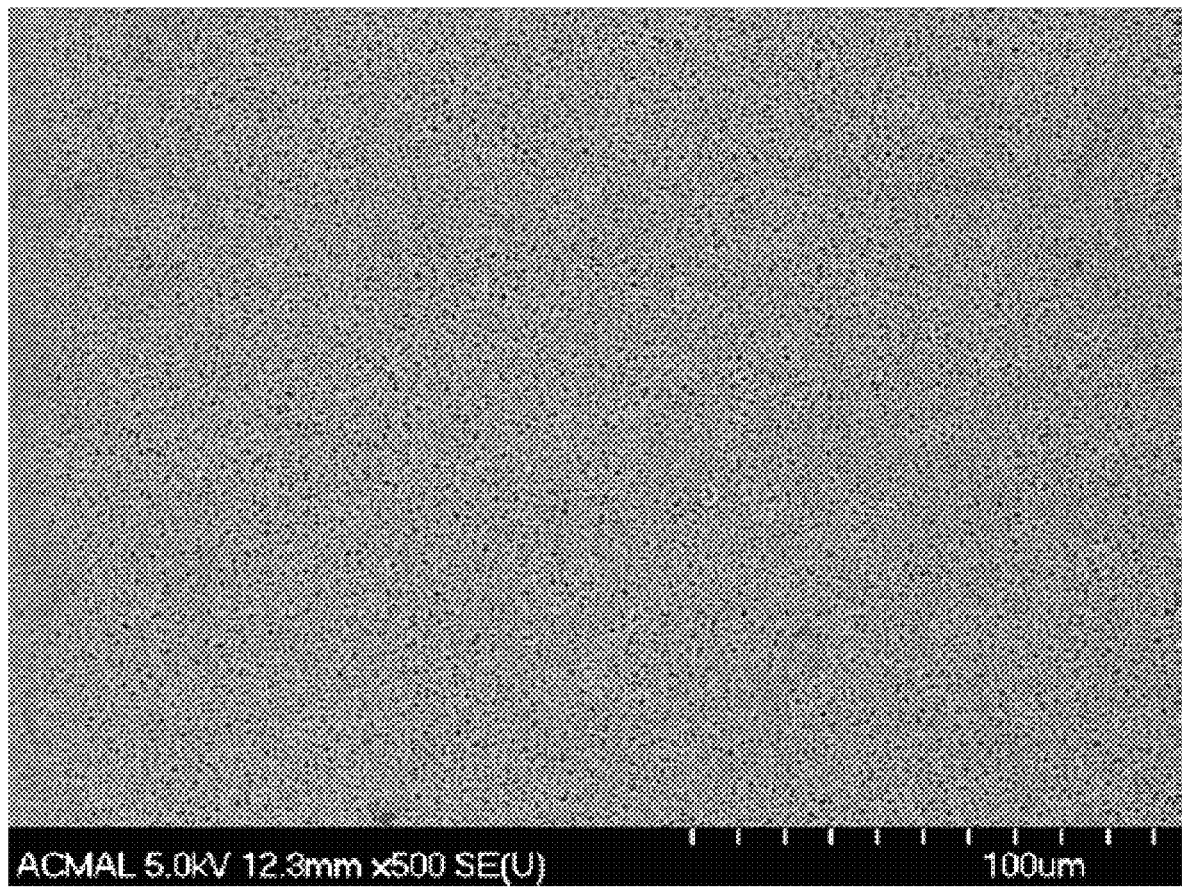
FIG. 7 shows an SEM image of the surface of the foam-like structure of a membrane comprising PVDF and PDMS.
Figure 8:
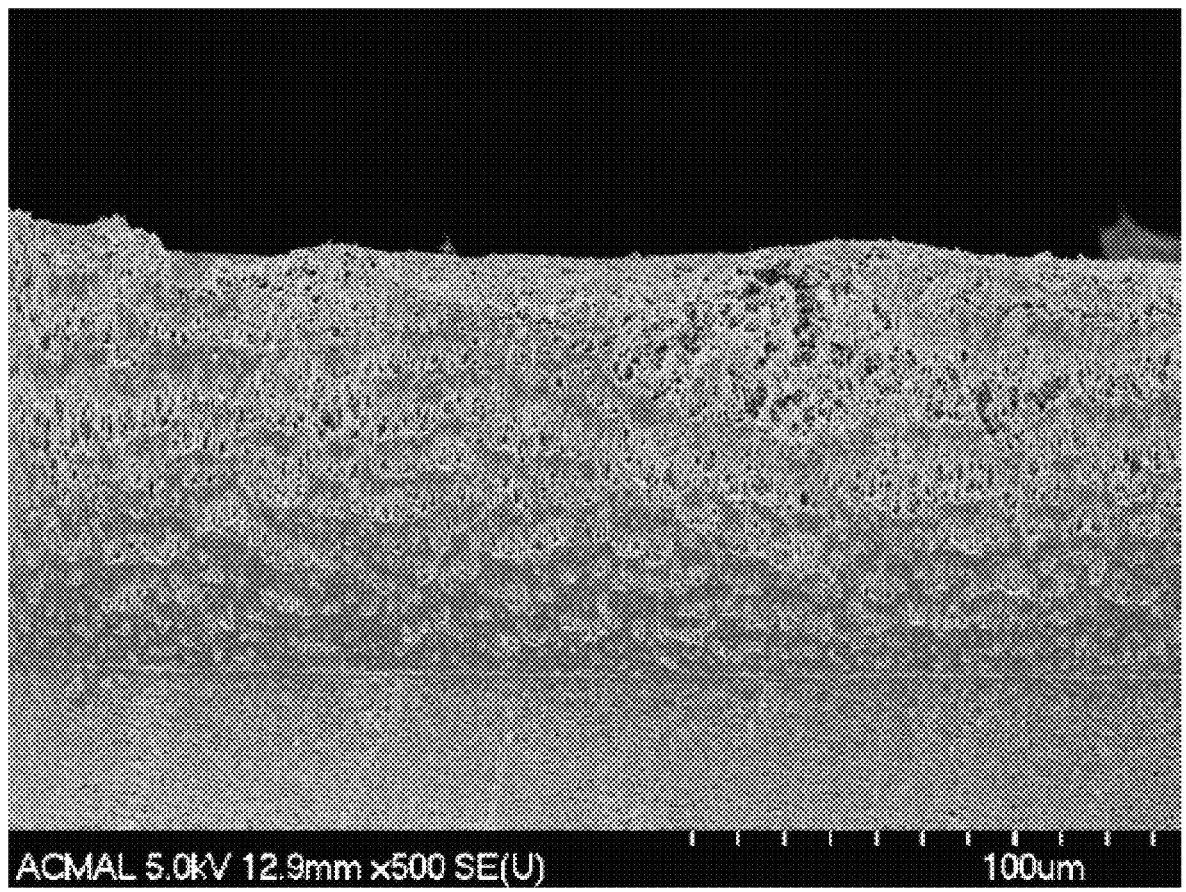
FIG. 8 shows an SEM image of the cross-section of the foam-like structure of a membrane comprising PVDF and PDMS.

The PVDF has a porous structure (FIGS. 7 and 8). The PDMS permeates at least a portion of the pores of the PVDF. In some embodiments, at least 99% of the pores of the PVDF are filled with PDMS.

To achieve real-time NO measurement, NO gas molecules need to pass through the membrane as fast as possible, so that it can be detected in real-time. The Einstein-Smoluchowski equation describes the net molecule displacement, $\Delta x$, versus time (t) as $(\Delta x)^2 = 2Dt$, where D represents the diffusion coefficient.

To get a small t value, a thin interface and large D are required. To achieve this, a diluted RTV-3140/Sylgards solution in toluene can be manually cast on PVDF layer by layer. A total of 3 layers is preferred. Total polymer thickness can be well controlled within 20 mm. To control and adjust the thickness of polymer layer, different concentration of RTV-3140 solution (0.1 g/ml and 0.125 mg/ml) and different number of layers cast can be used.

In one embodiment, the total coverage of PDMS is about 4 mg per square centimeter. In another embodiment, the total coverage of PDMS is less than about 4 mg per square centimeter. In yet another embodiment, the total coverage of PDMS is greater than about 4 mg per square centimeter.

In certain embodiments, the membrane has a thickness between about 15 µm and about 200 µm. The membrane may have a total thickness between about 15 and about 200, about 25 and about 190, about 35 and about 180, about 45 and about 170, about 55 and about 160, about 65 and about 150, about 75 and about 140, about 85 and about 130, about 95 and about 120, or about 100 and about 115 µm. The membrane have a total thickness less than or equal to about 200, about 175, about 150, about 125, about 100, about 75, about 50, about 25, about 20, or about 15 µm. The membrane may have a total thickness of about 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 µm.

Since PDMS is not a good cell culture substrate, a biocompatible polymer can be disposed on the membrane. Typically, an intermediate layer of adhesive is necessary between the PDMS and the biocompatible polymer.

ECM component gelatin, for example, can be used for surface treatment as a biocompatible polymer. To do this, PDMS can be surface treated by coating with dopamine, which serves as an intermediate adhesive, and further with a gelatin solution applied over the polydopamine layer to assist cell adhesion for cell culture. In this case, the layer of gelatin also protects the cells from being exposed to PVDF.

In certain embodiments, the biocompatible polymer is selected from the group consisting of gelatin, fibronectin, collagen, specific receptor proteins, antibodies, patterned DNA, electrospun fibers, cell adhesion matrixes or features, naturally or artificially laid down extracellular matrix, other cellular polymers, and combinations thereof.

In certain embodiments, the adhesive is selected from the group consisting of polydopamine, organosilanes, PDMS, modified PDMS, crosslinkers, carbodiimides, gluldahyde, and combinations thereof.

Figure 4:
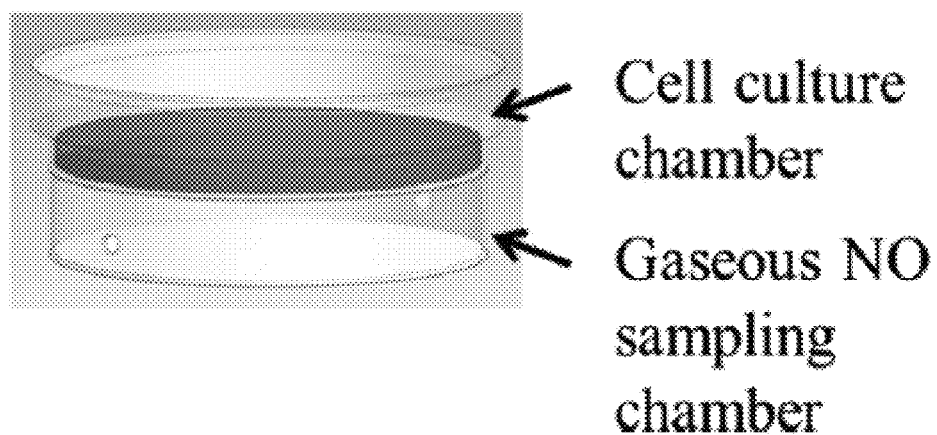
FIG. 4 shows an embodiment of a cell culture experiment set-up. Cells were seeded within a first (upper) chamber, the illustrated device was placed within a cell incubator for normal cell culture, and it was coupled to sampling lines that attached to a chemiluminescence NO detector.
Figure 5:
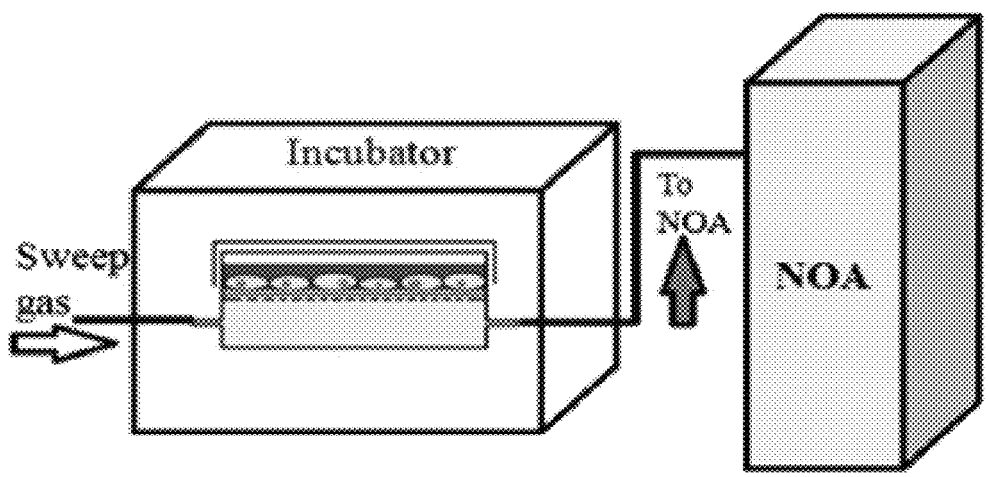
FIG. 5 shows an illustration of how NO sampling can be initiated and stopped at any time point during cell culture in this particular embodiment.

FIG. 4 illustrates the structure of an embodiment of the final device with a cell culture chamber on top and gas sampling chamber at the bottom. The assembled device can be coupled to a chemiluminescence detector and placed within an incubator for measuring real-time NO released from cells (FIG. 5).

The disclosed device achieves a real-time cellular gas measurement without disturbing the cells under investigation or deviating from standard cell culturing protocols. This device opens up a huge potential for increasing understanding of the role NO and other gases play in both normal and pathological conditions in a variety of tissues, and it could potentially accelerate the ability to design NO releasing and generating therapeutic interventions by allowing quantitative understanding of both the dose and temporal aspects of NO production in cells.

EXAMPLES

It should be kept in mind that the following described embodiments are only presented by way of example and should not be construed as limiting the inventive concept to any particular physical configuration.

Example 1

Cell Culture and Treatment

Mouse macrophage cell line (RAW264.7) was kept in culture in conventional polystyrene petri-dish within complete DMEM (with 10% FBS and 1% penicillin-streptomycin). Cells were scraped off and reseeded into the first (upper) chamber of the disclosed device. RAW264.7 cultured within complete media was used as the negative control. Cells were stimulated with LPS and/or IFN-γ. During NO measurement, different reagents which may change cellular NO generation profile were administrated to cultured cells such that the final concentration of the reagents are specified, including arginine (an additional 1 mM), the arginase inhibitor nor-NOHA (10 µM), and the NOS inhibitor L-NAME (50 µM).

Direct Measurement of NO Release from Cells

Cells were cultured within the first (upper) chamber using standard cell culturing conditions until confluent, unless otherwise stated. RAW264.7 cells were then stimulated with LPS and/or IFN-γ. The device containing cells was then placed into 37° C. 5% CO$_2$ incubator. The second (lower)

chamber of the device was connected to NOA. Cellular NO generation was measured in PPB/sec (parts per billion/s), converted to moles/sec, and normalized to surface area per time to determine the surface flux of NO released by the cell layer (nmole $cm^{-2}$ $min^{-1}$).

Cellular NO Probing by DAF

DAF-FM stain was dissolved in DMEM to the final concentration of 10 μM. The DAF-FM contained media was applied to cultured cells and incubated for 20 min at 37° C. with 5% $CO_2$. Media was removed and cells were washed twice with PBS; then submerged in PBS and imaged using either Zeiss AxioVert 200 M Apo Tome or Olympus BX51 fluorescent microscope.

Cell Image by Fluorescent Microscope

Cells were stained with live-dead assay reagents, 2 μM calcein-AM and 2 μg/ml ethidium bromide, in DMEM solution for 10 min. Fluorescently labeled cells were imaged via Zeiss AxioVert 200 M Apo Tome fluorescent microscope or Olympus BX51 microscope.

Membrane SEM and AFM Imaging

The prepared semi-permeable membrane was cross-sectioned into 0.5 cm pieces. The membrane was platinum coated (50 nm) and imaged with a Hitachi S-4700 FE-SEM. Polydopamine and gelatin treated membrane was cut into 0.5 0.5 cm pieces for topographic image by Veeco Dimension 3000 at. force microscope. The aluminum reflex coated cantilever (Tap300Al-G) was used with a resonance frequency of 300 kHz and a force constant of 40 N/m.

Statistical Analysis

The data was analyzed by either student's t-test or one-way analysis of variance. All statistical assays were achieved through R programming, unless specifically noted.

Fabrication of PVDF Membrane

First, a mixture of Dow Corning Sylgard 184 PDMS base and curing agent (10:1, w/w) dissolved in hexane was vortex-mixed to form 1:30 (w/v) PDMS solution.

Then, 1 mL of freshly prepared Sylgard solution was manually cast onto a 5 cm×5 cm square of PVDF membrane (Bio-Rad Immun-Blot for Protein Blotting) and allowed to air dry. This was repeated for a total of 3 times.

After the organic solvent had air dried, the membrane was carefully transferred to a drying oven at 50° C. overnight to cure the Sylgard polymer.

The composite membrane was then cut into a circle to fit inside a 60 mm diameter cell culture plate.

Then, the membrane was attached to the cell culture plate that had had its bottom removed (a 46 mm dia. circle was cut from the center of the bottom of the culture dish, leaving a 3 mm wide rim on the inside of the dish to which the membrane is attached to serve as the bottom of the culture dish) by wetting the culture dish rim with toluene and pressing the membrane to seal in softened polystyrene.

Then, the lower chamber was fabricated by drilling 2 holes in the sides of a second culture dish at 90° from each other (90-120° was used and confirmed to be sufficient) and epoxying 2 frits (Male luer lock barbs, 1/8" (3.2 mm) ID) into the holes. The epoxy was loctite 2-min, 2-part epoxy.

Then, the chambers were assembled together by aligning the upper and lower chambers and applying toluene dropwise to melt the plastic together.

Then, freshly prepared dopamine solution (2 mg/mL, in Tris-HCl buffer pH=8.5) was applied into the upper chamber, soaking for 24 h (12 to 20 h was sufficient, and no more than 24 h). The polydopamine coating needed exposure to ambient oxygen. The volume of dopamine solution (about 5 mL) needed to cover the membrane; excess solution was poured off and the surface was rinsed with DI water to remove any extra polydopamine particles that formed. The membrane was allowed to air dry.

Then, the chamber was sterilized by either ethylene oxide sterilization (24 h). Alternatively, the plate can be sterilized by filling with 70% ethanol for 15 min followed by 30 min of air drying and 1 hour of exposure to UV light in a bio safety cabinet.

The dopamine-coated membrane in the plate was then treated with a solution of gelatin (2 mg/mL Bio-Rad EIA Grade Reagent Gelatin, cat #170-6537, prepared from DI water and can be stored at 4 degree for up to one month) for 1 h. The volume of gelatin solution (about 5 mL) needed to cover the bottom of the plate. Excess solution was poured off. The device was air dried for 1 hour and then ready for cell culture use.

Two-Chamber NO Delivery Device Design

Figure 9:
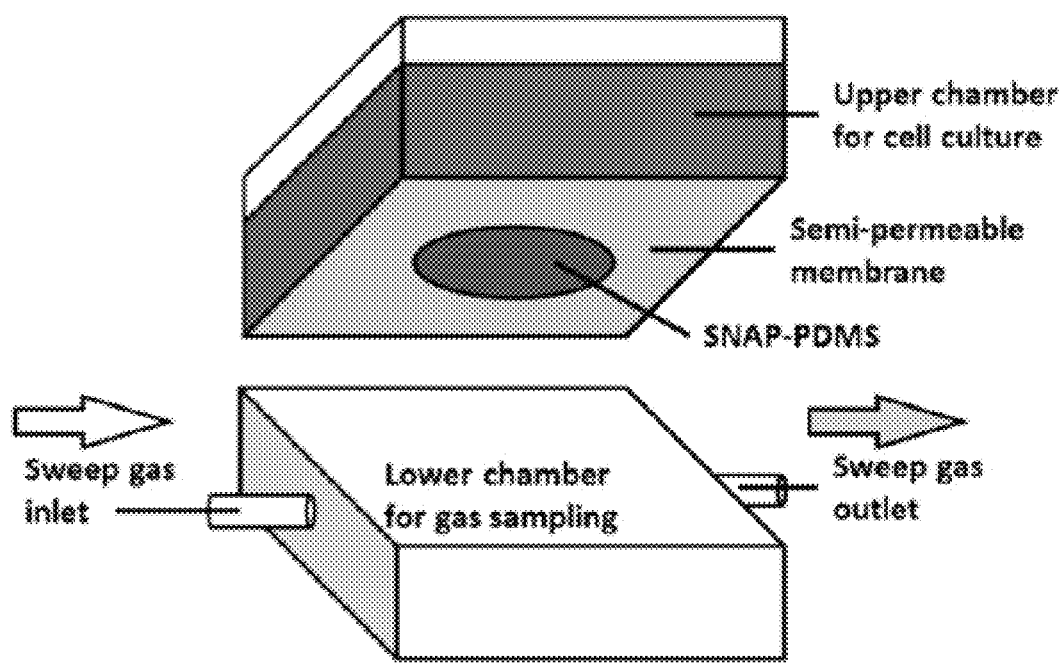
FIG. 9 shows an embodiment of a two-chamber device according to the present disclosure.

A NO delivery set-up was designed to achieve controlled, localized NO delivery (FIG. 9). Cells were grown on the membrane of the NO measurement system and NO releasing polymers were applied to the cultured cells from the other side of the membrane according to specific needs and then removed so that the NO flux was zero after a defined delivery time. By connecting this system to a chemiluminescence detector, actual NO delivered to the cells could be monitored. Ethidium bromide was introduced to label dead or dying cells for better understanding the cell status.

However, while RTV-3140 and glass fiber filter paper were used to fabricate the NO permeable but water tight gas-permeable NO membrane, there were some issues associated with the NO permeable membrane, including NO releasing polymer SNAP-PDMS could not be easily applied to the membrane and the quality of the fluorescent cell image and the stiffness of the produced film needed to be markedly improved for adhesive cells. Thus, the design of the NO measurement device was significantly altered.

Sylgard PDMS replaced RTV-3140 and reproducibly generated stiffer composite membranes. Glass-fiber filter paper was replaced by PVDF (polyvinylidene fluoride) membrane (pore size 2 μm). Compared with glass-fiber filter paper, PVDF has a finer fiber structure. After PDMS polymer was cast, the produced membrane displayed a more homogeneous and smooth surface, which is very important for fluorescent imaging. To manufacture the membrane, the mixture of Sylgard PDMS base and curing agent (10:1, w/w) dissolved in hexane was vortex-mixed to form 1:20 (w/v) PDMS solution. The solution was manually cast onto the PVDF membrane (72 μl/$cm^2$/cast) and air-dried. Three layers were cast to form a usable membrane. After the organic solvent was air-dried, the membrane was carefully transported into 52° C. heating oven for overnight curing. The micro structure of the produced gas-permeable membrane was examined by SEM, shown in FIGS. 7 and 8.

NO Delivery Device Fabrication

To manufacture the delivery device, a semipermeable membrane was attached to plastic boxes to form the upper chamber of the device for cell culture, as shown in FIG. 9. Dopamine solution (1 mg/ml, in Tris-HCl buffer pH=8.5) was applied into the upper chamber, soaking for 24 h to increase PDMS hydrophilicity; the chamber was ethylene oxide sterilized and top treated with 2 mg/ml gelatin solution for 1 h to facilitate cell adhesion. Then the device was ready for cell culture. The lower chamber was produced by adding 2 ports onto a plastic box, so that the device could be easily coupled into an NOA sampling line. Once the two chambers were placed together, with the SNAP-PDMS polymer disk attached directly under the membrane, NO was delivered into the upper chamber at a specified flux, which was simultaneously being quantified through sampling NO from the lower chamber, as shown the FIGS. 9 and 10, and adjusted by the light source underneath the device.

Because the actual level of NO being delivered to the cells was monitored in real-time, the NO generating rate could be modulated in real-time by adjusting light energy impinged on the polymer.

Since NO flux was mainly controlled by light, to create a system that will generate homogeneous NO across the whole NO source plane, a homogeneous light source was needed. A 7×7 LED light array using (VAOL-5GSBY4, Mouser, Tex.) LED bulb was fabricated. Blue light LED buds (593-VAOL-5GSBY4, Mouser) were tin-soldered onto the printed circuit board (PCB) to form a 7×7 LED array. An LED diffuser (Bright View Tech, Morrisville, N.C.) was placed over the LED array to homogenize the light. To evaluate how homogeneous the light from the source plane was, digital pictures of the light source plane were taken with a black foam board placed on top of the light source to avoid light leaking. ImageJ was used to analyze the digital photo of the light source and the light intensity distribution. The signal strength of each and every pixel of the picture indicated a good homogeneity of the light source.

Controllable NO Delivery Device Build-Up

To confirm that the NO signal measured in the lower chamber and the NO entering the upper chamber were linearly related and the change was synchronized, two identically calibrated NOAs were simultaneously used to measure NO flux in real-time from both chambers; different LED light intensity was used to manipulate the total NO flux such that different NO levels in both chambers at different time points were recorded in real-time. Linear regression analysis was performed to validate the relationship between the flux levels measured from both chambers.

NO released from SNAP-PDMS film either diffused into the cell culture device or remained in the lower chamber. The signal sampled by NOA did not actually represent the NO flux experienced by the cells (the idea is the same with the two-chamber NO measurement device).

The following experiment was completed to determine the relationship between the sampled NO flux and NO flux that the cultured cells experienced in the upper chamber. The SNAP-PDMS disk (4 mm diameter, about 340 µm thick) was placed under the PDMS membrane as the NO source. SNAP-PDMS film was exposed under linearly changed light intensity by changing LED drive current linearly to generate different total NO fluxes while NO in both chambers were recorded via two identically calibrated NOAs.

Figure 6:
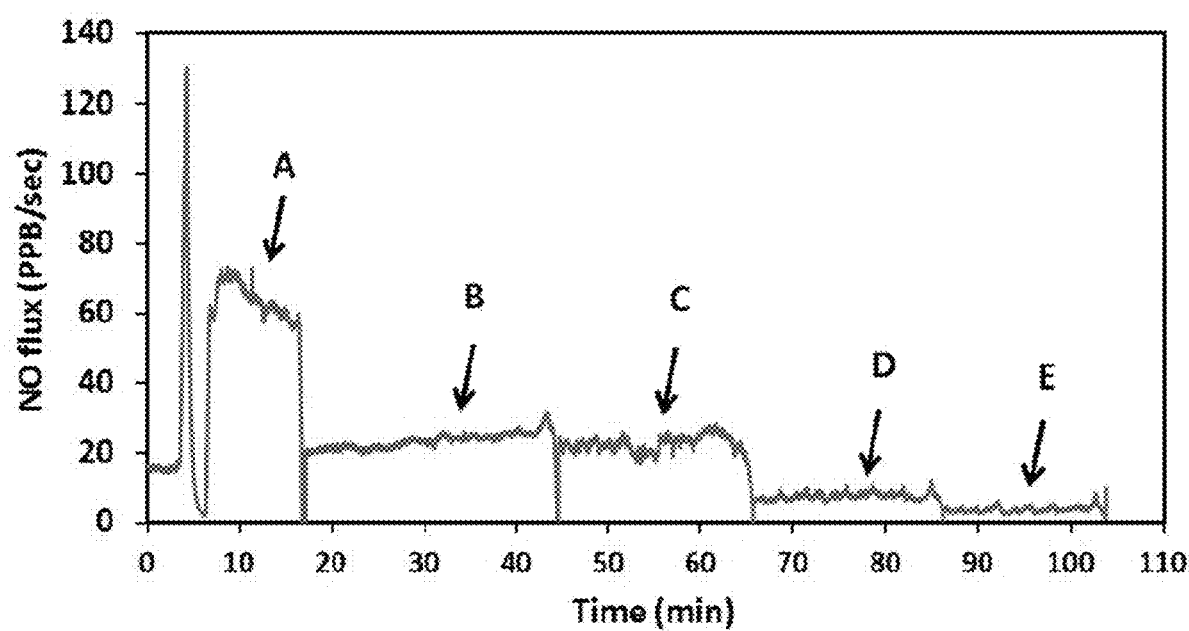
FIG. 6 shows how a NO flux measurement was influenced by the thickness of an NO permeable membrane. A SNAP-PDMS disc, which released NO at a specific flux rate (arrow A) was were inserted into aqueous solutions contained within the upper chambers of gas measurement devices of the present disclosure, where each device utilized a PVDF/PDMS membrane of differing thickness. The trans-membrane NO flux was measured for devices having membranes with a thickness of 17.3±3.2 μm (arrow B), 39.4±4.7 μm (arrow C), 53.8±6.2 μm (arrow D), and 162.3±9.5 μm (arrow E), respectively.

The NO flux pattern was recorded simultaneously (FIG. 6), and the linear regression analysis showed that NO signals in both chambers did change linearly with each other (R=0.9999). The difference of NO signals in the upper and lower chamber was observed and the distribution rate was determined by the geometry of NO releasing material, membrane properties, and the attachment. These results suggested that once there is NO generation in the lower chamber by using SNAP-PDMS attached to the NO permeable membrane, cells cultured on the upper chamber experienced NO immediately without time delay, and the NO signal captured from the lower chamber and the actual NO delivered into the upper chamber were linearly related.

Example 2

Control Over Membrane Properties

Since the sensitivity of the NO measurement method relies on restricting the thickness of PDMS layer, membranes with consistent thickness were manufactured. It was determined that a thinner polymer layer is better for NO permeability without allowing water leakage. Meanwhile, cell growth requires a certain level of overall membrane stiffness. If a material is too soft, cell migration and proliferation will be affected, which may introduce significant variability in behaviors of standard cell-line models. Accordingly, the properties of PDMS/PVDF layer were optimized.

Figures 10A, 10B, 10C, 10D, 10E:
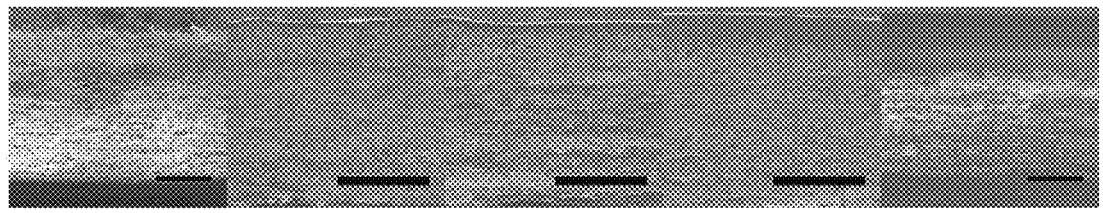
FIG. 10A, FIG. 10B, FIG. 10C, FIG. 10D, and FIG. 10E show cross-section SEM images of different thicknesses of PDMS membrane generated by multiply casting different concentrations of PDMS solutions (for each cast, 72 μl/cm$^2$ solution was applied), scale bar: 150 μm.

To optimize the thickness of PDMS necessary to provide water impermeability and still be thin enough to allow necessary gas diffusion, different numbers of membrane casting or different concentration of PDMS solutions were applied, controlling the amount of PDMS deposited on the membrane. RTV-3140 solutions were used to establish the thickness requirements (1 g/10 ml toluene and 1.25 g/10 ml toluene). By applying varying numbers of layers cast, NO permeable composite membranes with different thicknesses of PDMS were generated. FIG. 10 shows the control over the PDMS layer thickness imaged by SEM; B to E have different PDMS layer thicknesses, 17.3±3.2 µm, 39.4±4.7 µm, 53.8±6.2 µm, 162.3±9.5 µm, respectively.). This ensured water impermeability, but allowed gas diffusion.

To optimize the necessary stiffness of the membrane, Sylgard PDMS was used. Different from RTV-3140, the PDMS polymer base and the curing agent are supplied separately. By using a different base to curing agent ratio and different curing temperature, a silicone elastomer with different stiffness can be produced. For the following adhesive cell culture, a base: curing agent ratio of 10:1 (w/w) was used, and the curing condition was set to 52° C. overnight. This stiffness was appropriate for cell culturing and the thickness had sufficient water impermeability and gas diffusion to functionally allow the device to work.

To confirm that the NO signal measured in the lower chamber and the NO entering the upper chamber were linearly related and the change was synchronized, two identically calibrated NOAs were simultaneously used to measure NO flux in real-time from both chambers. Different LED light intensity was used to manipulate the total NO flux such that different NO levels in both chambers at different time points were recorded in real-time. Linear regression analysis was performed to validate the relationship between the flux levels measured from both chambers.

Example 3

Detection of Nitric Oxide in Human Dermal Fibroblast Cells

Diabetic foot ulcers (DFU) are a major health problem associated with diabetes mellitus. Impaired nitric oxide (NO) production has been shown to be a major contributor to the dysregulation of healing in DFU. However, the level of impairment is not known primarily due to challenges with measuring NO. The disclosed device was used to measure NO production in human dermal fibroblasts under normal and high glucose conditions.

Cell Culture and Chemical Supplies: Primary human adult dermal fibroblasts (HDFa, ATCC® PCS-201-012™), mouse macrophages (RAW 264.7), penicillin streptomycin, fetal bovine serum (FBS), phosphate buffered saline (PBS), 3-(4,5-dimethylthiazol-2-yl)-2,5-diphenyltetrazolium bromide (MTT) proliferation assay kit and Dulbecco's modified eagle medium (DMEM high glucose 4500 mg/L) were all purchased from ATCC (Manassas, Va., USA). DMEM (no glucose), sodium pyruvate and Hoescht dye were obtained from Fischersci (Hanover Park, Ill., USA). Lipopolysaccharide *pseudomonas aeroguinosa* (LPS), Calcein-AM, protease inhibitor cocktail, mouse nitric oxide synthase and dopamine-HCl were purchased from Sigma-Aldrich (St. Louis, Mo., USA). Ethidium bromide was acquired from Invitrogen (Grand Island, N.Y., USA). Human recombinant Interferon (hrIFN-γ) was purchased from GenScript (Piscataway, N.J., USA). The primary and secondary antibodies against CD90/Thy1 (ab23894) protein and (iNOS) (ab136918) were purchased from Abcam (Cambridge, Mass., USA). The 7.5% SDS polyacrylamide gels and gelatin were acquired from Bio-Rad (Hercules, Calif., USA). The Odyssey western blot starter kit 2 was obtained from LI-COR (Lincoln, Nebr., USA). Silicone elastomer base and curing agent (Dow Corning Sylgard® 184) were obtained from ML Solar LLC (Campbell, Calif., USA).

Real Time NO Measurements from Primary Human Adult Dermal Fibroblasts: Primary adult dermal fibroblasts at passage 1 were cultured and expanded in conventional cell culture plates (100 mm) in DMEM (high or normal glucose levels), 10% FBS and 1% penicillin/streptomycin (complete growth media). At confluency, the cells were reseeded in NO detection devices at a density of $0.25\text{-}1\times10^4$ cells/cm$^2$. The NO detection devices were generated as described herein. Briefly, silicone elastomer base and curing agent were dissolved in hexanes, manually cast onto 5×5 cm square polyvinylidene fluoride (PVDF) membranes and left to cure in a 50° C. oven for 24 h. The modified membrane was cut into a circle to fit into a 60 mm diameter cell culture plate with the bottom removed forming the upper chamber. The upper chamber was sealed by applying toluene to the edges of the membrane and the plate. A second 60 mm plate with drilled holes and plastic outlets attached was affixed to the upper chamber using toluene and reinforced with epoxy adhesive. The upper chamber was used for cell culture and the lower chamber was used for gaseous transfer. To make the device suitable for cell culture, freshly prepared dopamine solution in Tris-HCl buffer (2 mg/mL) was added to the device and incubated for 12 h. The device was rinsed several times and sterilized using 70% ethanol and ultraviolet light (1 h). Prior to cell culture, the device was coated with gelatin solution (2 mg/mL). After 24-72 hours, the cell culture media was changed and substituted with media containing 40 μg/ml of LPS and 200 U/mL of hrIFN-γ or complete growth media (control) under normal glucose (5.5 mM) and high glucose (25 mM) conditions. The device was placed in a standard incubator (37 C, 65% humidity, 5% $CO_2$) and was connected to a calibrated nitric oxide analyzer (NOA) and the real-time NO release profile was measured for 24 hours.

Cell Viability Assay. After 24 h, the live-dead assay was carried out using 2 μM calcein AM, 2 μg/mL ethidium bromide and 10 μg/mL Hoescht dye in DMEM media for 10-15 min. The cells were imaged and analyzed using an Olympus fluorescent microscope (model BX51) and Image J1 respectively.

Cell Proliferation Assays (MTT Assay): The fibroblast cells were cultured in 96 well plates at a density of 10,000 cells per well in normal and high glucose cell culture conditions and stimulated with 40 μg/mL and 200 U/mL of LPS and IFN respectively. At the end of 24, 48 and 72 h, MTT assay was performed according to the manufacturer's instructions (Trevigen, 4890-025-K, Gaithersburg, Md., USA) with minor modifications. Briefly, the cell culture media was replaced with 25 μL of the MTT reagent and incubated for 4 h to allow the intracellular reduction of soluble yellow MTT to insoluble formazan dye. The MTT reagent was discarded and 100 μL of Isopropyl alcohol was added to solubilize the dye. The absorbance was read at a wave length of 570 nm using a VERSAmax tunable microplate reader model (Molecular devices, Sunnyvale, Calif., USA).

Nitrite Assay: After 24 h of measurement in the CellNO trap device, the cell culture media from the cell samples under normal and high glucose conditions were collected. The triiodide assay was used to measure the nitrite accumulation in the media. Briefly, 50 μL of the media was added to a vial containing a stirring solution of 300 μL of glacial acetic acid and 120 μL of potassium iodide. The vial was connected to a calibrated Sievers Nitric Oxide Analyzer 280i (Zysense, LLC, Boulder, Colo., USA) and the NO produced from the nitrite present in the media was measured and normalized to the number of live cells.

Cell Characterization: Fibroblast cells at passage 2 were cultured in 12 well plates at a cell density of $1\times10^4$/cm$^2$ in normal and high glucose conditions. At confluency, the cells were fixed in 4% paraformaldehyde for 10 min, rinsed three times in phosphate buffered saline, incubated in blocking buffer for 90 min followed by the primary antibody for 18 h at 4° C. The cells were rinsed three times in blocking buffer and incubated for 1 h at room temperature with the secondary antibody, stained with 4',6-diamidino-2-phenylindole (DAPI) and viewed under a fluorescent microscope.

Western Blot Analysis: Confluent HDFa cells were cultured in 100 mm diameter tissue culture dishes, stimulated with 40 μg/mL of LPS and 200 U/mL IFN-γ in normal and high glucose conditions and incubated for 72 h. Mouse macrophage cells RAW 264.7 were grown to confluency and stimulated with 100 ng/mL of LPS for 18 h and served as the positive control. The cells were quickly washed in ice cold PBS, trypsinized, centrifuged and re-suspended in 200 μL of RIPA buffer in the presence of protease cocktail inhibitors. The cell lysates were incubated for 30 min on ice on a plate shaker and centrifuged at 12,000 rpm for 20 min at 4° C. The supernatant was collected and the protein concentration determined for each sample using Bradford assay. An equal amount of loading buffer containing dithiothreitol was added to each sample, boiled at 100° C. for 5 min and immediately placed on ice for 2 min. About 5.63-9.37 μg of protein was loaded in a 7.5% SDS-PAGE gel and separated by electrophoresis at 100 V for approximately 70 min. The proteins were transferred to Immobilon®-FL PVDF membrane using the Trans-Blot® Turbo™ Transfer System (Bio-Rad) for 7 min. The membrane was incubated in Odyssey blocking buffer (TBS) for 60 min to block nonspecific binding sites followed by incubation in TBS containing 0.2% of tween20 (TBS-T) and the iNOS antibody (1:1000 dilution) for 18 h at 4° C. After that, the membrane was washed 4 times with TBS (0.1% tween20) and incubated in TBS-T with the secondary antibody (1:20,000 dilution) for 1 h then extensively washed in TBS, visualized by LI-COR Odyssey infrared imager and analyzed using Image Studio Lite software Version 5.2. Statistical analysis was performed in Microsoft Excel using one-way ANOVA followed by a Bonferroni corrected t-test with statistical significance set at a 95% confidence level ($p<0.05$).

Figure 11:
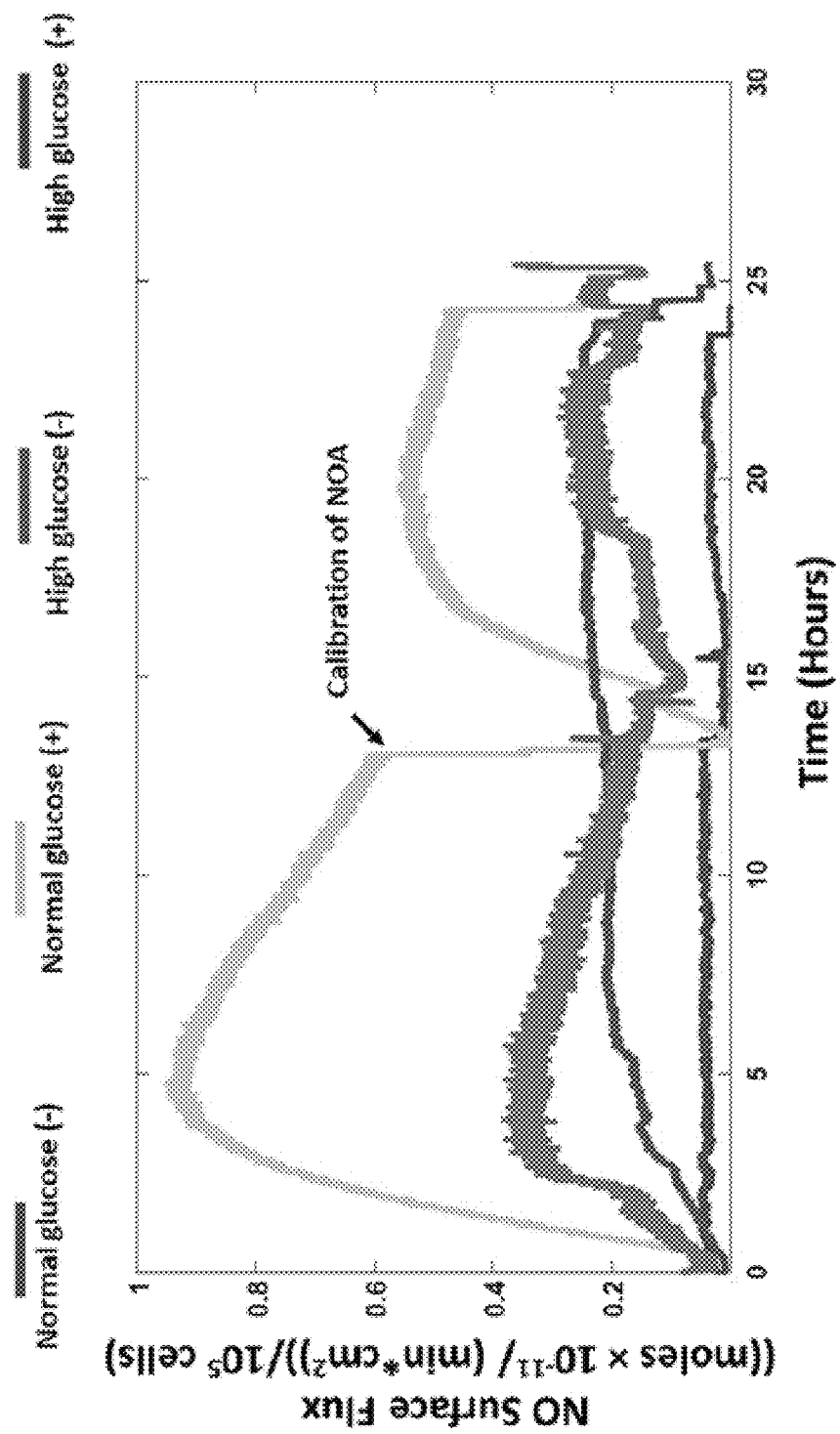
FIG. 11 shows a graph of real-time nitric oxide (NO) surface flux (normalized to the cell number) generated from HDFa with (+) and without (−) stimulation cultured under normal (5.5 mM) and high glucose (25 mM) conditions measured with chemiluminescence detection using an NO detection device disclosed herein.

Real-Time NO Detected under Normal and High Glucose Conditions: Primary human adult dermal fibroblasts were cultured in the NO detection device in either normal (5.5 mM) or high glucose (25 mM) media with and without stimulation by the inflammatory cytokine interferon gamma (IFN-γ) and bacterial endotoxin lipolysaccharide (LPS). The NO production was measured for 24 h (FIG. 11). The cells cultured in normal glucose media in the absence of stimulation showed a slight increase in NO release in the first 1 h which peaked at $0.5\times10^{-12}$ (moles/min·cm$^2$)/$10^5$ cells and remained constant for 24 h. The HDFa cultured in high glucose media without stimulation showed an increase in NO production which peaked at $0.19 \times 10^{-11}$ (moles/min·cm$^2$)/10$^5$ cells and remained constant for 24 h. With stimulation, there was an increase in the NO production for cells cultured in normal glucose media, which peaked at $0.94 \times 10^{-11}$ (moles/min·cm$^2$)/10$^5$ cells and gradually dropped to $0.6 \times 10^{-11}$ (moles/min·cm$^2$)/10$^5$ cells. At 13 h, the NOA was disconnected and recalibrated to confirm the validity of the signal obtained (Arrow denoting the sudden drop in curve in FIG. 11). The NO detected remained fairly constant around $0.5 \times 10^{-11}$ (moles/min·cm$^2$)/10$^5$ cells up to 24 h. The NO release for cells cultured in high glucose media followed a similar trend but with lower NO detected, which peaked at $0.35 \times 10^{-11}$ (moles/min·cm$^2$)/10$^5$ cells at approximately 4 h and gradually dropped to $0.81 \times 10^{-12}$ (moles/min·cm$^2$)/10$^5$ cells for 24 h.

Figure 13:
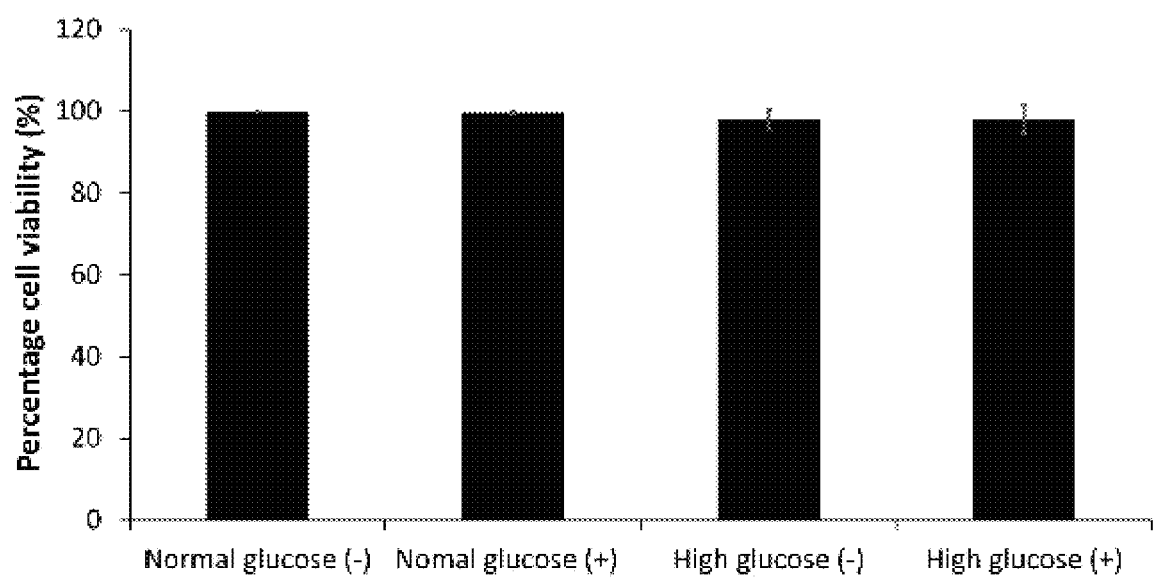
FIG. 13 is a bar graph quantifying the results presented in FIG. 12A, FIG. 12B, FIG. 12C, and FIG. 12D.

The viability of the cells cultured in the NO detection device in normal and high glucose culture conditions with and without stimulation by IFN-γ and LPS was analyzed by the live/dead assay at the end of the real-time NO measurements. Cell viability detected by calcein AM and ethidium bromide for primary human adult dermal fibroblasts (HDFa) cultured in normal (5.5 mM) glucose condition with and without stimulation, (FIG. 12A,B) respectively and high glucose (25 mM) condition without and with stimulation (FIG. 12C,D) respectively. The cells maintained over 95% cell viability in all the treatment groups (FIG. 13).

Figure 14:
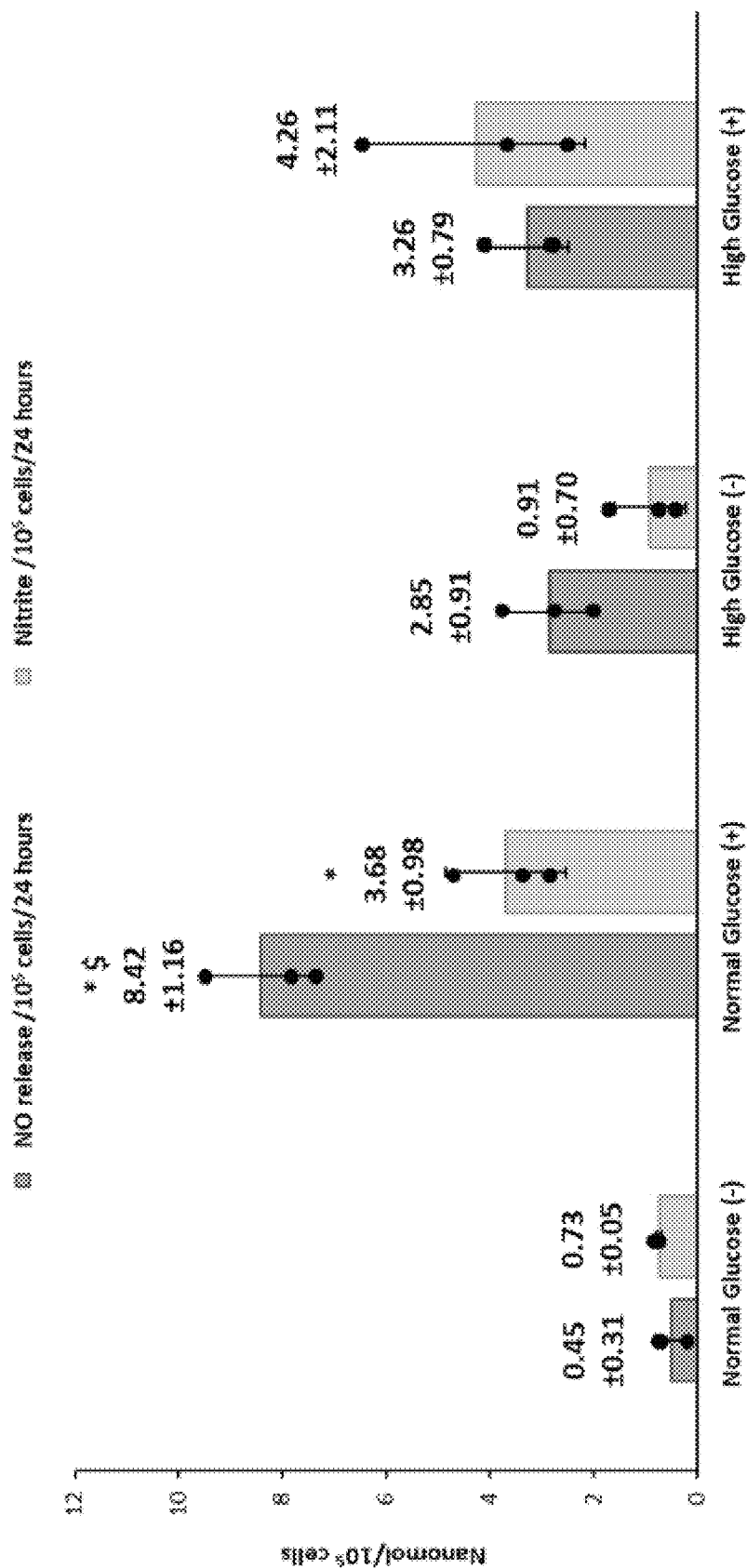
FIG. 14 is a bar graph showing total NO compared to nitrite accumulation determined for HDFa with and without stimulation under normal and high glucose conditions. For N=3, there is statistically significant difference at p<0.05. * normal glucose (LPS/IFN) vs. normal glucose (without stimulation); $ normal glucose (LPS/IFN) versus high glucose (LPS/IFN), dots on each average bar indicate individual data points.

Nitric Oxide Detected from Nitrite Accumulation in the Absence and Presence of Stimulation: After the real-time NO measurements, the cell culture media was collected and analyzed for nitrite using the triiodide assay (FIG. 14). The nitrite present in the media is reduced in the presence of an acid and nucleophile to produce NO that is measured via chemiluminescence detection. Normal glucose conditions without stimulation had significantly lower NO levels produced from nitrite compared to normal glucose conditions with stimulation (0.73+/−0.05 versus 3.68+/−0.98 nmol/105 cells, p<0.05 for n=3). In high glucose conditions, there was no statistical difference in the levels of NO detected without stimulation compared to stimulation with LPS/IFN (0.91+/−0.70 versus 4.26+/−2.11 nmol/10$^5$ cells). In the absence of stimulation, the NO detected from nitrite in normal glucose conditions compared to high glucose were not significantly different (0.73+/−0.05 versus 0.91+/−0.70 nmol/10$^5$ cells). Similarly, with stimulation, the NO detected from nitrite was not statistically different in normal glucose compared to high glucose 3.68+/−0.98 versus 4.26+/−2.11 nmol/10$^5$ cells.

Comparison of Real-Time NO Measurements and Nitrite Accumulation: The total NO detected in real-time for the HDFa was determined by integrating the area under the curve (FIG. 11) and was compared to the NO inferred from nitrite present in the cell culture media for the 4 treatments groups (FIG. 14). The results showed that the levels of real-time NO detected in nmol/10$^5$ was significantly higher for cells in normal glucose conditions with stimulation (8.42+/−1.16 p<0.05 for n=3) compared to without stimulation (0.48+/−0.31 for n=3 p<0.05). Similarly, under identical conditions, nitrite accumulation was significantly higher in normal glucose with stimulation (3.68+/−0.98) compared to absence of stimulation (0.73+/−0.05 for n=3 p<0.05). It is interesting to note that there was a higher direct NO measured compared to nitrite. However, high glucose conditions did not show the same trend. The levels of real-time NO detected with stimulation were not statistically different from levels of real-time NO without stimulation (3.26+/−0.79 and 2.85+/−0.91 nmol/10$^5$ cells respectively).

The NO levels obtained from nitrite measurement depicted a similar trend as the real-time NO measured, with no statistical difference in high glucose conditions with stimulation compared to high glucose without stimulation (4.26+/−2.11 and 0.91+/−0.70 nmol/10$^5$ cells). The real-time levels of NO and nitrite detected in normal glucose conditions without stimulation were also not statistically different from the real time NO detected from the cells in high glucose conditions without stimulation (0.48+/−0.31 and 3.26+/−0.79 versus 0.73+/−0.05 and 0.91+/−0.70 nmol/10$^5$ cells respectively for n=3 p<0.05). Moreover, in normal glucose conditions with stimulation, the levels of real-time NO detected was significantly higher compared to high glucose conditions with stimulation. The nitrite levels were not statistically different. (8.42+/−1.16 and 3.26+/−0.79 versus 3.68+/−0.98 and 4.26+/−2.11 nmol/10$^5$ cells respectively).

Figure 15B:
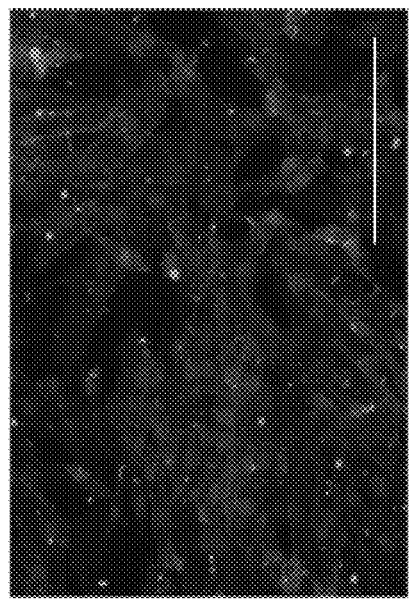
FIG. 15A and FIG. 15B are images showing immunofluorescent staining of CD90 (green) in HDFa cultured in normal (FIG. 15A) and high glucose (FIG. 15B) conditions. Cell nuclei are shown in blue. Scale bar 200 μm.
Figure 15A:
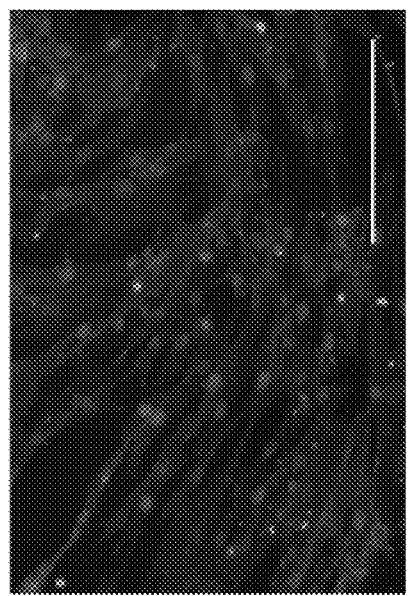

Cell Characterization of HDFa Cultured in Normal and High Glucose Conditions: Primary human adult dermal fibroblasts cultured in normal and high glucose media were assessed for the presence of CD90 (Thy-1), which is a reliable molecular marker used to identify fibroblast cells in culture. The HDFa maintained uniform staining for CD90 protein in normal (FIG. 15A) and high glucose conditions (FIG. 15B) as well as the elongated and spindle shape that is characteristic of confluent fibroblast cells.

Figure 16:
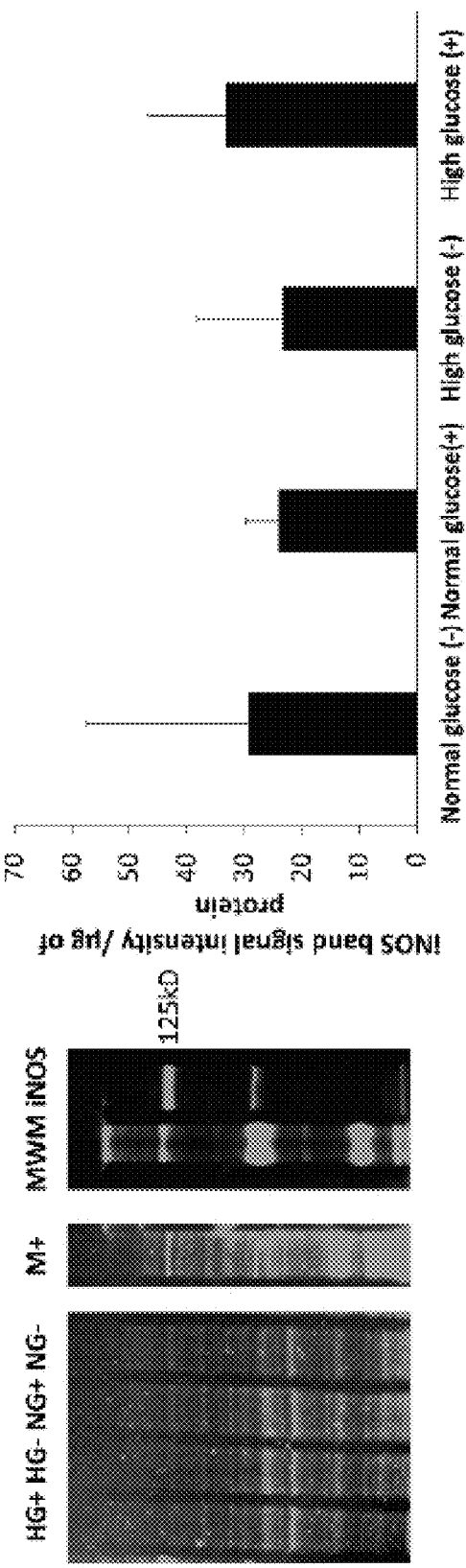
FIG. 16 is a western blot (left) and bar graph (right) showing detection of iNOS expression by western blot analysis of HDFa cultured in normal (NG) and high glucose (HG) conditions with (+) and without (−) stimulation. Predicted band size for iNOS 131 kD and observed band size 125 kD with iNOS and RAW 264.7 (M+ as positive controls. MWM—molecular weight marker. Results are quantified in the bar graph.

Expression of iNOS Protein in HDFa Cultured in Normal and High Glucose Conditions: Stimulation of fibroblasts by inflammatory cytokines and bacterial endotoxins has been reported to upregulate the enzyme iNOS, which is directly responsible for the production of NO in the cells. The levels of iNOS in HDFa were assessed in cells cultured in normal and high glucose conditions with and without stimulation by western blot. The results show that overall the iNOS enzyme was present in all treatment groups and the protein level was very low. Macrophage cell lysates (RAW 264.7) that are known to express iNOS when stimulated with LPS and the mouse iNOS enzyme protein were used as positive controls. Faint iNOS bands can be seen in the human fibroblasts cells, which appear at the same molecular weight as the iNOS in macrophage cells and the mouse iNOS enzyme (FIG. 16). There was no statistical difference in intensity found between the groups at p<0.05 for n=3.

Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

In its broadest definition, the term "dispersion" is intended to include homogeneous solutions, heterogeneous solutions, suspensions, colloids, aerosols, sols, emulsions, gels, emulsions, foams, and combinations thereof. A dispersion may also refer to any one of the aforementioned phases, or it may refer to any one of the possible combinations of the aforementioned phases. For example, a dispersion could include homogeneous solutions, heterogeneous solutions, suspensions, colloids, and emulsions but exclude aerosols, sols, and gels.

The terms "comprise(s)", "include(s)", "having", "has", "can", "contain(s)", and variants thereof, as used herein, are intended to be open-ended transitional phrases, terms, or words that do not preclude the possibility of additional acts or structures. The singular forms "a", "and", and "the" include plural references unless the context clearly dictates otherwise. The present disclosure also contemplates other embodiments "comprising", "consisting of", and "consisting essentially of", the embodiments or elements presented herein, whether explicitly set forth or not.

The conjunctive term "or" includes any and all combinations of one or more listed elements associated by the conjunctive term. For example, the phrase "an apparatus comprising A or B" may refer to an apparatus including A where B is not present, an apparatus including B where A is not present, or an apparatus where both A and B are present. The phrase "at least one of A, B, ... and N" or "at least one of A, B, ... N, or combinations thereof" are defined in the broadest sense to mean one or more elements selected from the group comprising A, B, ... and N, that is to say, any combination of one or more elements A, B, ... or N including any one element alone or in combination with one or more of the other elements, which may also include, in combination, additional elements not listed.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4". The term "about" may refer to plus or minus 10% of the indicated number. For example, "about 10%" may indicate a range of 9% to 11%, and "about 1%" may mean from 0.9-1.1. Other meanings of "about" may be apparent from the context, such as rounding off, so, for example "about 1" may also mean from 0.5 to 1.4.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

Various features and advantages of the invention are set forth in the following claims.

What is claimed is:

1. A device comprising:
   a first chamber;
   a second chamber; and
   a membrane permeable to neutral gases but impermeable to water that is positioned between the first chamber and the second chamber;
   wherein the membrane includes a first layer comprising PVDF and PDMS, wherein the PVDF has a plurality of pores at least partially filled with at least some of the PDMS;
   wherein the membrane includes a second layer comprising a biocompatible polymer disposed on the first layer between the first layer and the first chamber;
   wherein the biocompatible polymer is selected from the group consisting of gelatin, fibronectin, collagen, specific receptor proteins, antibodies, patterned DNA, electrospun fibers, cell adhesion matrixes or features, extracellular matrix, and combinations thereof.

2. The device of claim 1, wherein the second layer is adhered to the first layer with an adhesive.

3. The device of claim 2, wherein the adhesive is selected from the group consisting of polydopamine, organosilanes, PDMS, modified PDMS, crosslinkers, carbodiimides, gluldahyde, and combinations thereof.

4. The device of claim 1, wherein the membrane has a thickness between about 15 µm and about 200 µm.

5. The device of claim 1, wherein the second chamber is in fluid communication with a gas detection or gas measurement device.

6. The device of claim 5, wherein the gas detection or gas measurement device is adapted to measure or detect a gas selected from the group consisting of $NO_{(g)}$, $N_{2(g)}$, $CO_{2(g)}$, $O_{2(g)}$, $H_2O_{2(g)}$, $CO_{(g)}$, $H_2S_{(g)}$, $NH_{3(g)}$, and combinations thereof.

7. The device of claim 5, wherein the gas measurement or gas detection device comprises a chemiluminescent detection device, an electrochemical detection device, an optical detection device, an infrared spectroscopy device, a mass spectrometry device, a gas chromatography device, or a quartz crystal microbalance.

8. A method for detecting or measuring the amount of a neutral gas associated with an aqueous solution, comprising:
   providing the aqueous solution in the first chamber of the device of claim 1;
   collecting a sample of the neutral gas from the second chamber of the device; and
   detecting or measuring the amount of the neutral gas in the sample with a gas measurement or gas detection device.

9. The method of claim 8, wherein the gas measurement or gas detection device is in the second chamber.

10. The method of claim 8, wherein the gas measurement or gas detection device is outside the second chamber.

11. The method of claim 10, wherein collecting the sample comprises moving the sample from the second chamber to the gas measurement or gas detection device using a sweep gas.

12. The method of claim 11, wherein the sweep gas comprises nitrogen or ambient air.

13. The method of claim 8, wherein the aqueous solution contains living cells.

14. The method of claim 13, further comprising culturing the living cells in the aqueous solution.

15. The method of claim 8, wherein the aqueous solution further contains a polymer.

16. The method of claim 15, wherein the polymer is a hydrogel.

17. The method of claim 15, wherein the polymer is adapted to release nitric oxide.

* * * * *